US009056894B2

(12) United States Patent
Lihme et al.

(10) Patent No.: US 9,056,894 B2
(45) Date of Patent: Jun. 16, 2015

(54) METHODS FOR CAPTURING VIRUS LIKE PARTICLES FROM PLANTS USING EXPANDED BED CHROMATOGRPAHY

(75) Inventors: Allan Lihme, Copenhagen (DK); Karen Oishi, Neuchatel (CH); Inga Vaarst, Copenhagen (DK); Rosa Cabrera, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 13/881,499

(22) PCT Filed: Oct. 27, 2011

(86) PCT No.: PCT/EP2011/068919
§ 371 (c)(1),
(2), (4) Date: Jun. 25, 2013

(87) PCT Pub. No.: WO2012/055986
PCT Pub. Date: Mar. 5, 2012

(65) Prior Publication Data
US 2013/0317197 A1    Nov. 28, 2013

(30) Foreign Application Priority Data
Oct. 27, 2010   (EP) .................................. 10014019

(51) Int. Cl.
*C07K 1/18*     (2006.01)
*C07K 14/42*    (2006.01)
*B01D 15/18*    (2006.01)
*B01D 15/36*    (2006.01)

(52) U.S. Cl.
CPC .............. *C07K 1/18* (2013.01); *B01D 15/1807* (2013.01); *B01D 15/363* (2013.01); *C07K 14/42* (2013.01)

(58) Field of Classification Search
None
See application file for complete search history.

(56) References Cited

FOREIGN PATENT DOCUMENTS

EP          1 104 479      10/2006
WO    WO 2004/082397       9/2004

OTHER PUBLICATIONS

D'Aoust et al. "Influenza virus-like particles produced by transient expression in *Nicotiana benthamiana* induce a protective immune response against a lethal viral challenge in mice" Plant Biotechnology Journal (2008) 6, pp. 930-940.*
PCT International Search Report and Written Opinion dated Nov. 29, 2011 for PCT/EP2011/06819.
Menkhaus et al. "Compatibility of Column Inlet and Absorbent Designs for Processing of Corn Endosperm Extract by Expanded Bed Absorption", *Biotechnology and Bioengineering*, vol. 87, No. 3, Aug. 5, 2004 (pp. 324-336).
Bai et al., "Capture of a Recombinant Protein from Unclarified Canola Extract Using Streamline Expanded Bed Anion Exchange", *Biotechnology and Bioengineering*, vol. 18, No. 7, Mar. 30, 2003, pp. 855-864.
Bertrand, et al., "Expanded Bed Chromatography for One-Step Purification of Mannose Binding Lectine from Tulip Bulbs Using Mannose Immobilzed on DEAE Streamline", *Journal of Chromatography A.*, vol. 822, No. 1, Sep. 25, 1998, pp. 19-28.

* cited by examiner

*Primary Examiner* — Suzanne M Noakes
*Assistant Examiner* — Gerard Lacourciere
(74) *Attorney, Agent, or Firm* — Mueting, Raasch & Gebhardt, P.A.

(57) ABSTRACT

The present invention relates to a method for capturing virus-like particles of interest from a mixture comprising the use of an expanded bed of adsorbent; suitably wherein said method comprises the steps of: (a) providing an expanded bed of adsorbent; (b) contacting the mixture with the adsorbent such that the constituents of the mixture contact the expanded bed of adsorbent; (c) optionally washing the adsorbent; and (d) optionally eluting the particle of interest from the adsorbent.

19 Claims, No Drawings

METHODS FOR CAPTURING VIRUS LIKE PARTICLES FROM PLANTS USING EXPANDED BED CHROMATOGRPAHY

This application is a U.S. National Stage Application of International Application No. PCT/EP2011/068919, filed Oct. 27, 2011, which was published in English on May 3, 2012 as International Patent Publication WO 2012/055986. International Application No. PCT/EP2011/068919 also claims priority to European Application No. 10014019.3, filed Oct. 27, 2010.

FIELD OF THE INVENTION

The present invention relates to the capture of a particle of interest—such as a virus like particle (for example, a recombinantly expressed, self-assembled VLP)—from a mixture.

The invention allows for the efficient capturing of particles of interest which can be scaled up to large volumes for use on a commercial scale.

INTRODUCTION

The genetic engineering revolution has expanded to the development of recombinant proteins that can be used in a variety of different applications, including human and animal therapeutics. There are well over 100 biotechnology-derived therapeutics and vaccines approved by the U.S. FDA for medical use and over 1000 additional drugs and vaccines are in various phases of clinical trials. Bacterial, yeast, insect, plant and mammalian cell expression systems are currently used to produce recombinant proteins, with varying degrees of success. Although this development in technology has revolutionized the production and delivery of pharmaceutical and therapeutic products, problems still remain with purifying the molecules that can be obtained. For example, purifying protein from bacteria requires the lysis of cells which may require several steps and solution clarification. Chromatographic resins used in the purification process are then prone to clogging and cell extracts may require further clarification by other processes—such as centrifugation or filtration. Multiple stages of purification may also be required which takes time and can also lead to the loss of sample and reduced yields. Purification of a protein of interest can be expensive and technically challenging. The downstream processing can comprise up to 80 percent of the entire cost.

Packed bed adsorption chromatography is widely employed for the purification of proteins. Use of packed beds requires removal of whole cells or colloidal debris. Though often ignored in the development of the laboratory scale process, the removal of debris is one of the most challenging operations to achieve with high efficiency. Expanded bed adsorption is a recently developed methodology which can be used to purify soluble protein and places less demand on the clarification of the process stream. It uses the flow of fluid through an initially packed bed structure to achieve contact with a high fluid voidage.

One approach for producing recombinant protein, especially immunogenic recombinant protein—such as immunogenic viral recombinant protein—has been to use virus like particles (VLPs). Many viruses have capsids that can assemble from the individually expressed structural proteins, both in vivo within the cell where the structural proteins and recombinant proteins are expressed in forming VLPs, and outside of the cell after isolation and purification. However, the capturing of such VLPs in a mixture containing high suspended solids content and particles of varying sizes, typically in situations involving plant-derived materials, are technically very challenging. VLPs may be immunogenic when injected into animals to induce the production of anti-viral antibodies that can block infection. Thus, for example, mice vaccinated with virus-like particles produced with proteins from an H5N1 avian strain can be protected against challenge with lethal H5N1 viruses.

There remains a need in the industry for a method of capturing particles of interest with improved efficiency and yield. There is also a need for such a method to be scaleable for the commercial level to capture of particles of interest in a cost effective manner.

SUMMARY OF THE INVENTION

The present invention is based, at least in part, on the discovery that Expanded Bed Adsorption (EBA) chromatography is particularly efficient for the capture of a particle of interest from a mixture. In certain embodiments, the method can advantageously be used for the capture of a particle of interest in a one step binding and elution process that is scaleable to commercial levels.

In a general aspect, there is provided a method for capturing a particle of interest from a mixture comprising the use of an expanded bed of adsorbent.

In one embodiment, the method comprises the steps of: (a) providing an expanded bed of adsorbent; (b) contacting the mixture with the adsorbent such that the constituents of the mixture contact and interact with the expanded bed of adsorbent; (c) optionally washing the adsorbent; and (d) optionally eluting the particle of interest from the adsorbent.

In one embodiment or a combination of the above-mentioned embodiment(s), the particle of interest is a biological particle of interest.

In one embodiment or a combination of the above-mentioned embodiment(s), the particle of interest comprises at least one protein.

In one embodiment or a combination of the above-mentioned embodiment(s), the particle of interest comprises at least two proteins, at least one of which is a protein of interest.

In one embodiment or a combination of the above-mentioned embodiment(s), the particle of interest is a virus like particle.

In a first aspect of the invention, there is provided a method for capturing virus like particles of interest from a mixture comprising the use of an expanded bed of adsorbent; suitably wherein said method comprises the steps of: (a) providing an expanded bed of adsorbent; (b) contacting the mixture with the adsorbent such that the virus like particles in the mixture bind the adsorbent; (c) optionally washing the adsorbent; and (d) optionally eluting the virus like particles from the adsorbent.

In one embodiment of this first aspect, the invention further relates to a method according to the preceding embodiment or a combination of the above-mentioned embodiment(s), wherein the virus like particles comprises a protein of an influenza virus, particularly a haemagglutinin; suitably a haemagglutinin subtype selected from the group consisting of H1, H2, H3, H4, H5, H6, H7, H8, H9, H10, H11, H12, H13, H14, H15 or H16 or a combination of two or more thereof.

In one embodiment or a combination of the above-mentioned embodiment(s) including an embodiment of this first aspect, the adsorbent is contained in a column.

In one embodiment or a combination of the above-mentioned embodiment(s) including an embodiment of this first aspect, the mixture is or is derived from a plant.

In one embodiment or a combination of the above-mentioned embodiment(s) including an embodiment of this first aspect, the plant is a naturally occurring plant, a mutant plant, a non-naturally occurring plant or a transgenic plant.

In one embodiment or a combination of the above-mentioned embodiment(s), the mixture is or is derived from a leaf of a plant.

In one embodiment or a combination of the above-mentioned embodiment(s) including an embodiment of this first aspect, the mixture is produced by homogenising plant material prior to contact with the adsorbent. Thus, according to this embodiment, the mixture is homogenised plant material.

In one embodiment or a combination of the above-mentioned embodiment(s) including an embodiment of this first aspect, the plant is a plant cell—such as a plant cell grown in culture or outside of a plant such as in vitro grown plant cells or clumps of cells—such as carrot cells.

In one embodiment of the first aspect of the invention, the invention provides a method according to any of the preceding embodiments or a combination of the preceding embodiment(s), wherein the mixture comprises disrupted cells of a plant; suitably wherein the plant is a tobacco plant infiltrated with nucleic acid molecules that express a protein transiently in the plant, said protein being present in the virus like particles; more suitably wherein the mixture is or is derived from aerial parts of the plant.

In one embodiment or a combination of the above-mentioned embodiment(s) including an embodiment of this first aspect, the adsorbent comprises a plurality of beads.

In one embodiment or a combination of the above-mentioned embodiment(s) including an embodiment of this first aspect, the beads are composite beads that comprise an inert core material.

In one embodiment or a combination of the above-mentioned embodiment(s) including an embodiment of this first aspect, the beads comprise, consist or consist essentially of a material selected from the group consisting of plastics, methacrylate, an anion exchanger, diethylaminoethyl, a cation exchanger, a polysaccharide, silica, poly(styrenedivinyl)benzene, polyacrylamide, ceramic and derivatives thereof or a combination of two or more thereof.

In one embodiment or a combination of the above-mentioned embodiment(s) including an embodiment of this first aspect, the beads comprise, consist or consist essentially of a polysaccharide; suitably cellulose, agarose, dextran, or derivatives thereof, or a combination of two or more of the foregoing.

In one embodiment or a combination of the above-mentioned embodiment(s) including an embodiment of this first aspect, the inert core material comprises, consists or consists essentially of a material selected from the group consisting of quartz, silica, Nd—Fe—B alloy, stainless steel, zirconium oxide, zirconia, metal silicates, metal borosilicates, ceramics including titanium diboride, titanium carbide, zirconium diboride, zirconium carbide, tungsten carbide, silicon carbide, aluminium nitride, silicon nitride, titanium nitride, yttrium oxide, silicon metal powder, and molybdenum disilicide; metal oxides and sulfides, including magnesium, aluminium, titanium, vanadium, chromium, zirconium, hafnium, manganese, iron, cobalt, nickel, copper and silver oxide; non-metal oxides; metal salts, including barium sulphate; metallic elements, including tungsten, zirconium, titanium, hafnium, vanadium, chromium, manganese, iron, cobalt, nickel, indium, copper, silver, gold, palladium, platinum, ruthenium, osmium, rhodium and iridium, and alloys of metallic elements, such as alloys formed between said metallic elements and derivatives thereof or a combination of two or more thereof.

In one embodiment or a combination of the above-mentioned embodiment(s) including an embodiment of this first aspect, the size of the beads is between about 5 µm and 500 µm or more.

In one embodiment or a combination of the above-mentioned embodiment(s) including an embodiment of this first aspect, the size of the beads that bind the particle of interest is between about 25 µm and 100 µm; suitably about 50 µm.

In one embodiment or a combination of the above-mentioned embodiment(s) including an embodiment of this first aspect, the size of the beads that bind material other than the particle of interest, for example, plant materials, is between about 125 µm and 250 µm; suitably about 150 µm.

In one embodiment or a combination of the above-mentioned embodiment(s) including an embodiment of this first aspect, the method comprises a pre-capture step which comprises the use of an additional expanded bed of adsorbent. This first expanded bed of adsorbent comprises beads; suitably of a size range that is between about 125 µm and 250 µm; more suitably about 150 µm.

In one embodiment or a combination of the above-mentioned embodiment(s) including an embodiment of this first aspect, the adsorbent comprises a ligand.

In one embodiment or a combination of the above-mentioned embodiment(s) including an embodiment of this first aspect, the ligand comprises, consists or consists essentially of a ligand selected from the group consisting of (i) benzylamine or a derivative thereof; (ii) an alkylamine or a derivative thereof; (iii) an alkenylamine or a derivative thereof; (iv) an alkynylamine or a derivative thereof; (v) an alkoxyamine or a derivative thereof; and (vi) an amine of mono- or bicyclic aromatic or heteroaromatic moities or a derivative thereof, or a combination of two or more thereof.

In one embodiment or a combination of the above-mentioned embodiment(s) including an embodiment of this first aspect, the ligand comprises, consists or consists essentially of an anion exchange resin.

In one embodiment or a combination of the above-mentioned embodiment(s) including an embodiment of this first aspect, the anion exchange resin comprises, consists or consists essentially of or is a diethylaminoethyl cellulose-based ion exchange resin; suitably a diethylaminoethyl cellulose dextran-based ion exchange resin.

In one embodiment or a combination of the above-mentioned embodiment(s) including an embodiment of this first aspect, the conductivity of the mixture prior to contact with the adsorbent is between about 1 mS/cm and 10 mS/cm; suitably 2 mS/cm to 3 mS/cm.

In one embodiment or a combination of the above-mentioned embodiment(s) including an embodiment of this first aspect, the pH of the mixture prior to contact with the adsorbent is between about pH 6.0 and pH 8.0.

In one embodiment or a combination of the above-mentioned embodiment(s) including an embodiment of this first aspect, the mixture is loaded onto the column at a linear flow rate in the range of between about 1 cm/min and 15 cm/min to bind the particle of interest.

In one embodiment or a combination of the above-mentioned embodiment(s) including an embodiment of this first aspect, the density of the adsorbent is in the range of between about 1 g/ml and 20 g/ml.

In one embodiment or a combination of the above-mentioned embodiment(s) including an embodiment of this first aspect, the degree of expansion of the expanded bed is in the range of from about 1 to 5.

In one embodiment or a combination of the above-mentioned embodiment(s) including an embodiment of this first aspect, said method comprises a pre-capture step prior to contacting the mixture with the adsorbent.

In one embodiment or a combination of the above-mentioned embodiment(s) including an embodiment of this first aspect, the pre-capture step is selected from the group consisting of filtration, microfiltration, centrifugation, decantation and sedimentation or a combination of two or more thereof.

In one embodiment or a combination of the above-mentioned embodiment(s) including an embodiment of this first aspect, the pre-capture step comprises: (i) contacting the material with an ion exchange resin; or (ii) acid precipitating and filtering the material.

In one embodiment or a combination of the above-mentioned embodiment(s) including an embodiment of this first aspect, the material is contacted with the ion exchange resin in static binding or batch incubation mode.

In one embodiment or a combination of the above-mentioned embodiment(s) including an embodiment of this first aspect, the eluate or one or more fractions thereof obtained in step (d) is subjected to a further treatment step.

In one embodiment or a combination of the above-mentioned embodiment(s) including an embodiment of this first aspect, the further treatment step is selected from the group consisting of purification, filtration, microfiltration, centrifugation, decantation and sedimentation or a combination of two or more thereof.

In one embodiment or a combination of the above-mentioned embodiment(s) including an embodiment of this first aspect, the particle of interest comprises a protein of interest.

In one embodiment or a combination of the above-mentioned embodiment(s) including an embodiment of this first aspect, the protein of interest is an antigen.

In one embodiment or a combination of the above-mentioned embodiment(s) including an embodiment of this first aspect, the protein of interest is haemagglutinin.

In one embodiment or a combination of the above-mentioned embodiment(s) including an embodiment of this first aspect, the haemagglutinin is a haemagglutinin subtype selected from the group consisting of H1, H2, H3, H4, H5, H6, H7, H8, H9, H10, H11, H12, H13, H14, H15 or H16 or a combination of two or more thereof.

In one embodiment or a combination of the above-mentioned embodiment(s) including an embodiment of this first aspect, the expansion rate of the expanded bed during the elution step is between about 0.5 and 5.

In a second aspect, there is provided a method for capturing a particle of interest from a mixture comprising the steps of: (i) providing an expanded bed of adsorbent comprising a ligand in a column at a settled bed height of above 10 cm, wherein the density of the adsorbent is between about 1 g/ml and 20 g/ml, wherein the degree of expansion of the expanded bed is between about 1 and 5 and wherein the average adsorbent particle size is between about 5 μm and about 500 μm; (ii) equilibrating the resin material at a pH in the range of about pH 6.0 and 8.0; (iii) providing a mixture comprising the particle of interest, wherein said mixture has a conductivity of between about 1 mS/cm and 10 mS/cm; (iv) loading the mixture onto the column at a flow rate (for example, linear flow rate) in the range of between about 1 cm/min and 15 cm/min to bind the particle of interest; (v) washing the loaded column using a buffer having a pH in the range of about pH 6.0 and 8.0; and (vi) eluting the bound particle of interest from the column in one or more fractions.

In one embodiment of this second aspect, the particle of interest is a virus like particle (VLP) or a ghost-like particle.

In one embodiment or a combination of the above-mentioned embodiment(s) of this second aspect, the mixture is or is derived from a plant.

In one embodiment or a combination of the above-mentioned embodiment(s) of this second aspect, the plant is a naturally occurring plant, a mutant plant, a non-naturally occurring plant or a transgenic plant.

In one embodiment or a combination of the above-mentioned embodiment(s) of this second aspect, the mixture is or is derived from a Leaf of a plant.

In one embodiment or a combination of the above-mentioned embodiment(s) of this second aspect, the particle of interest comprises a protein of interest.

In one embodiment or a combination of the above-mentioned embodiment(s) of this second aspect, the protein of interest is an antigen.

In one embodiment or a combination of the above-mentioned embodiment(s) of this second aspect, the protein of interest is haemagglutinin.

In one embodiment or a combination of the above-mentioned embodiment(s) of this second aspect, the haemagglutinin is a haemagglutinin subtype selected from the group consisting of H1, H2, H3, H4, H5, H6, H7, H8, H9, H10, H11, H12, H13, H14, H15 or H16 or a combination of two or more thereof.

In one embodiment or a combination of the above-mentioned embodiment(s) of this second aspect, the size of the beads that bind the particle of interest is between about 25 μm and 100 μm; suitably about 50 μm.

In one embodiment or a combination of the above-mentioned embodiment(s) of this second aspect, the size of the beads that bind material other then the particle of interest, for example, plant materials, is between about 125 μm and 250 μm; suitably about 150 μm.

In one embodiment of this second aspect, or a combination of the above-mentioned embodiment(s) of this second aspect, a method is provided for capturing virus like particles of interest from a mixture comprising the steps of:

(i) providing an expanded bed of adsorbent comprising diethylaminoethyl cellulose dextran in a column, wherein the density of the adsorbent is between about 2.5 g/ml and 3.5 g/ml, and wherein the average adsorbent particle size is about 50;
(ii) equilibrating the resin material at a pH in the range of about pH 6.0 and 8.0;
(iii) providing a mixture comprising tobacco plant material, wherein said mixture has a conductivity of between about 2 mS/cm and 3 mS/cm;
(iv) loading the mixture onto the column at a flow rate of about 2.5 cm/min to bind the virus like particles and wherein the degree of expansion of the expanded bed in the column is about 2;
(v) washing the loaded column using a buffer having a pH in the range of about pH 6.0 and 8.0; and
(vi) eluting the bound particle of interest from the column in one or more fractions.

In one embodiment, the method of the preceding embodiment, or a combination of the above-mentioned embodiment(s) of this second aspect, comprises a step (iii) comprising (a) providing whole tobacco plants that are transiently expressing a protein that is present in the virus like particles; (b) disrupting cells of the leaves and stems of the tobacco plants to produce the tobacco plant material; and (c) adjusting the pH and conductivity of the mixture by dilution with a buffer or deionized water.

In one embodiment, the method of the preceding embodiment, or a combination of the above-mentioned embodiment(s) of this second aspect, comprises prior to step (iv), a step comprising filtering the mixture of step (iii) and contacting the filtered mixture of step (iii) with a first expanded bed of adsorbents comprising polyethylenimine, wherein the size of beads is about 150 μm, to remove undesired substances from the mixture.

In a third further aspect, there is provided an expanded bed of adsorbent comprising a particle of interest reversibly bound thereto.

In one embodiment of this third aspect, the adsorbent comprises a plurality of beads.

in one embodiment or a combination of the above-mentioned embodiment(s) of this third aspect, the size of the beads that bind the particle of interest is between about 25 μm and 100 μm; suitably about 50 μm.

In a fourth further aspect, there is provided the use of an expanded bed of adsorbent for capturing a particle of interest, particularly a virus like particle of interest from a mixture, more particularly a mixture which is derived from a plant that is transiently expressing a protein, said protein being present in the virus like particle.

In one embodiment of this fourth aspect, the particle is a virus like particle (VLP) or a ghost-like particle.

A fifth aspect relates to an expanded bed of adsorbent comprising a particle of interest; suitably a virus like particle of interest reversibly bound thereto, particularly wherein the adsorbent is in expanded bed chromatography mode.

A sixth aspect relates to the use of expanded bed chromatography for capturing a particle of interest; suitably a virus like particle; from a mixture.

The embodiment(s) and combinations of embodiments described above for the general and the first aspect of the invention may also form embodiments of at least the second, third, fourth, fifth and sixth aspects of this invention.

Definitions

The technical terms and expressions used within the scope of this application are generally to be given the meaning commonly applied to them in the pertinent art of plant and molecular biology. All of the following definitions apply to the complete content of this application. The word "comprising" does not exclude other elements or steps, and the indefinite article "a" or "an" does not exclude a plurality. A single step may fulfill the functions of several features recited in the claims. The terms "essentially", "about", "approximately" and the like in connection with an attribute or a value particularly also define exactly the attribute or exactly the value, respectively. The term "about" in the context of a given numerate value or range refers to a value or range that is within 20%, within 10%, or within 5% of the given value or range. The terms "parts per million" or "ppm" are used interchangeably herein to refer to a measure of purity of the particle of interest or protein of interest purified. The units ppm refer to the amount of host protein in nanograms/milliliter per protein of interest in milligrams/milliliter, where the proteins are in solution, host protein ppm=(host protein ng/ml)/(protein of interest mg/ml)]. Where the proteins are dried, such as by lyophilization, ppm refers to (host protein ng)/(protein of interest mg).

The term "expanded bed" relates to embodiments wherein the chromatographic process operates with a bed of adsorbents of classified (stratified) size ranges, density ranges, or both, stably fluidized by a directed liquid flow; suitably an upward liquid flow, with minimal axial mixing of the adsorbents, allowing both liquid and solid components in the liquid to contact the adsorbents while migrating through the bed. Suitably, the liquid migrates through the bed in a nearly plug-flow condition.

An "adsorbent" refers to any substance that can adsorb a particle of interest onto its surface by intermolecular forces. Typically the binding of the particle of interest to the adsorbent will be reversible such that it can be eluted from the adsorbent at a desired time.

As used herein, the term "particle of interest" refers to a molecular entity the capture of which from a mixture is desirable. In certain embodiments, the particle of interest comprises one or more proteins. In other embodiments, a particle of interest comprises one or more or two or more (for example, a plurality) of proteins, at least one of which is a protein of interest. In one embodiment, the particle to be captured is a particle comprising a plurality of macromolecules of biological origin and is therefore a biological particle of interest. In another embodiment, the particle to be captured is a virus like particle. In another embodiment, the particle to be captured is a bacterial ghost particle. As used herein, the term "captured particle of interest" refers to a preparation of particles of interest in which at least about 10%, 20%, 30%, 40%, 50%, 55%, 60%, 65%, 70%, 75%, 80%, 85%, 90%, 95%, 96%, 97%, 98%, 99% or 100% by weight of the preparation is the desired particle of interest. In embodiments, the methods of the present invention capture at least 50% of the total amount of particles of interest initially present in the mixture, including at least 60%, 70%, 80% or 90% of the particles of interest. Even higher capture rates may be achieved—such as at least 92.5%, 95%, 96%, 97%, 98% or at least 99%. The term "purified particles of interest" refers to a preparation of particles of interest in which at least about 50%, 55%, 60%, 65%, 70%, 75%, 80%, 85%, 90%, 95%, 96%, 97%, 98%, 99% or 100% by weight of the preparation is the desired particles of interest with the remaining weight being contributed by contaminating impurities or contaminants, particularly other proteins, nucleic acids, lipids or carbohydrates or a combination thereof—such as those derived from the host cell—which may copurify with the purified particles of interest. In one embodiment, the captured or purified particles of interest are substantially free from contaminating macromolecules (exclusive of solvent). The particles described herein may be characterised by various methods that are known in the art—such as electrospray differential mobility analysis (ES-DMA), asymmetric flow field-flow fractionation with multi-angle light scattering detection (AFFFF-MALS) and transmission electron microscopy (TEM). In one embodiment, the particle of interest measures less than about 1.0, 0.9, 0.8, 0.7, 0.6, 0.5, 0.4, 0.3, 0.2, 0.1, 0.09, 0.08, 0.07, 0.06, 0.05, 0.04 or 0.03 μm in diameter—such as 1.0 to 0.03, 0.8 to 0.03, 0.6 to 0.03, 0.4 to 0.03, 0.2 to 0.03, 0.1 to 0.03, 0.08 to 0.03, 0.06 to 0.03, 0.05 to 0.03 or 0.04 to 0.03 μm in diameter.

As used herein, the term "virus like particle" (VLP), "virus-like particles" (VLPs) or VLP of interest refers to molecular entities that are formed by self-assembly and comprises a plurality of proteins, including at least one protein of interest, and that in at least one attribute resembles a virus. Notably, unlike viral particles or virions, VLPs lack viral genomic nucleic acids. VLPs may have polydiversed, multimodal size distributions where the size distribution can be affected by changes in the production process. For example, the size distribution of VLPs produced in plants may be different to the size distribution of VLPs produced in different hosts. In embodiments, the VLPs (for example, VLPs captured from plant material) may have an average diameter of 35 nm, 40 nm, 45 nm, 50 nm, 55 nm, 60 nm, 65 nm, 70 nm or 75 nm. In embodiments, the diameter of VLPs captured (for example, from plant material) using the methods of the present invention is in the range of from 35 nm to 75 nm; suitably 35 nm to 70 nm; more suitably 35 nm to 65 nm; even more suitably 35 nm to 60 nm; particularly suitably 35 nm to 55 nm; even more particularly suitably 35 nm to 50 nm; further more suitably 35 nm to 45 nm; most suitably 35 nm to 40 nm.

As used herein, a "mixture" comprises a particle of interest together with one or more materials that are unwanted, such as impurities or contaminants. The terms "impurity" and "contaminant" are used interchangeably to mean any material, other than the particle of interest, regardless of whether it originates from a host organism, for which it is desirable to have removed from a composition comprising the particle of interest. The mixture can be obtained directly from a host organism or host cell that is producing the particles of interest. Without intending to be limiting, examples of mixtures that can be treated according to a method of the present invention include a feedstock, disrupted host cell materials, host tissue homogenate, host tissue lysate, host tissue extract, fermentation broth, and host cell culture supernatant. Impurities may include, but are not limited to, any biological macromolecule such as proteins other than the protein of interest, particles other than particles of interest that may comprise the protein of interest, nucleic acids (for example, DNA and RNA), lipids, polysaccharides (for example, starches, cellulose), lignin, phenolics, carbohydrates and pigments.

A "conditioned mixture" is a mixture that has been prepared for a chromatography step used in a method of the invention by subjecting the mixture to one or more of buffer exchange, dilution, salt addition, pH titration, or a combination of the foregoing in order to set the pH, conductivity range, buffer condition or a combination respectively to achieve a desired chromatography performance. A "conditioned mixture" can be a feedstock and can be used to standardize loading conditions onto the chromatography column.

The term "protein of interest", which is used interchangeably herein with the term "target protein", refers to one or more recombinantly produced protein(s) that is present in the particle of interest and that may be captured with the particle of interest as unassembled protein, multimeric forms of the protein, or partially assembled particle.

The term "host protein" refers to any of the proteins derived from the cells of the host that produce the particle(s) of interest that comprise the target protein, and includes any proteins expressed from the genome of the host or proteins that are recombinantly expressed, and which are not a constituent of the particle of interest. The amount of host protein present in a mixture comprising at least the particle of interest or protein of interest provides a measure of the degree of purity. Typically, the amount of host protein in a protein mixture is expressed in parts per million relative to the amount of the particles of interest or protein of interest in the mixture.

The term "capture" and grammatical variations thereof are used interchangeably herein to mean the retention or gathering of particles of interest from a mixture, resulting in a higher concentration of the particles of interest than the concentration in the mixture. The capture of the particles of interest from a mixture may be incomplete. The particles of interest captured can be a fraction of the total particles of interest in the mixture, such as but not limited to about 2%, 5%, 10%, 20%, 25%, 30%, 40%, 50%, 60%, 70%, 75%, 80%, or 90% or more.

The terms "purify" and "isolate" and grammatical variations thereof are used to mean the separation or removal, whether completely or partially, of at least one impurity from a mixture, which thereby improves the level of purity of a particle of interest in the composition. The protein of interest may be purified to achieve a composition which contains less than 100 ppm host protein and suitably less than 90 ppm, less than 80 ppm, less than 70 ppm, less than 60 ppm, less than 50 ppm, less than 40 ppm, less than 30 ppm, less than 20 ppm, less than 10 ppm, or less than 5 ppm host protein, as determined typically by ELISA.

A "ligand" can be used to capture one or more particles of interest or proteins of interest that bind it specifically. Suitably, a biologically specific ligand is covalently attached to an adsorbent or a solid support which forms the stationary phase of a chromatographic system and is accessible to the particles of interest or protein of interest present in the mobile phase. The particles of interest or protein of interest retains its specific binding affinity for the ligand during the chromatographic steps, while other solutes and proteins in the mixture do not bind appreciably or specifically to the ligand. Binding of the particles of interest or the protein of interest to the ligand in the stationary phase allows contaminants or impurities in the mobile phase to pass through the expanded bed while the particle of interest or the protein of interest remains specifically bound to the ligand. The specifically bound particle of interest or protein may be eluted from the ligand. By way of example, this may be achieved using low pH, high pH, low salt, high salt, competing ligand, or the like or even a combination of one or more thereof, and passes through the expanded bed with an elution buffer.

The terms "specific binding" and "binding specificity" describe the generally specific and reversible interactions between a particle of interest or a protein of interest and a ligand. The ligand may have chemically modifiable groups which allow it to be attached to an adsorbent or a solid support without destroying its binding activity. The ligand will typically have an affinity for the particle of interest or protein in the range of 10E+4 to 10E+8 M in free solution.

The term "plant" refers to any plant at any stage of its life cycle or development, and its progenies. The plant may be a naturally occurring, mutant, non-naturally occurring or transgenic plant. The plant may be infiltrated with nucleic acid molecules that encode a protein and express the protein in the infiltrated plant. Such infiltrated plant is not a transgenic plant because the nucleic acid molecules are not required to be inserted into the plant genome and transmitted into progenies. The term "plant cell" refers to a structural and physiological unit of a plant. The plant cell may be in farm of a protoplast without a cell wall, an isolated single cell, a cultured cell, a clump of two or more cells or as a part of higher organized unit such as but not limited to, plant tissue, a plant organ, or a whole plant. The term "plant material" refers to any solid, or liquid composition, or a combination thereof, obtained or obtainable from a plant, including leaves, stems, roots, flowers or flower parts, fruits, pollen, egg cells, zygotes, seeds, cuttings, secretions, extracts, cell or tissue cultures, or any other parts or products of a plant. In one embodiment, the plant material is or is derived from a leaf—such as a green leaf.

If ranges are provided herein, the maximum values on the lower and upper side of the range are meant to be included in said range. For example, if a range of between about 125 μm and 250 µm is provided, this range is meant to include the maximum values 125 µm and 250 µm, respectively.

DETAILED DESCRIPTION

The invention provides methods for capturing a particle of interest from a mixture by expanded bed adsorption. The particle of interest comprises one or more protein(s) of interest, one or more of which may be recombinantly produced by a host cell.

Expanded bed adsorption (EBA) is a unit operation that combines solid-liquid separation and product purification. The process operates with a bed of adsorbents of different sizes, density, or both that is expanded with an upward liquid flow. In various embodiments, the column is designed to avoid turbulence and excessive liquid mixing, especially backmixing along the axis of the column, while the individual beads are kept in a non-fixed, dynamic state moving narrowly only in a local zone in the column. The expanded beds may have a small mixing zone in the bottom part of the column where incoming liquid is distributed throughout the cross-section of the column; suitably expanded beds operate generally under plug flow conditions. The process allows both liquid and solid components in a feedstock to contact and interact with the adsorbents thereby allowing the performance of multi-stage chromatographic separation in a column. The bed expansion allows solid particles in the feedstock to pass through the bed differentially thereby providing a clarification function.

In traditional packed bed chromatographic methods, where the resin is confined between the bottom of a column and a flow adapter, clogging occurs when particulate matter and cell debris cannot flow around the closely packed resin. In contrast, the flow of liquid in EBA is fed from below, and the adapter is held away from the packed resin level, giving the adsorbents room to expand and thus creating spaces therebetween. The degree of expansion of the bed is affected by the flow rate of the mixture, the viscosity of the mixture as well as the density of the adsorbents. When the adsorbents are packed in the column, it sits close together and leaves little room for large aggregates and clumps to manoeuvre. As buffer is injected from below, the adsorbents become fluidized and form a stable concentration gradient when the sedimentation velocity of the adsorbents equals the upward liquid flow velocity. Various formats of EBA are available, some of which comprise a filtering means at the base of the column and others which do not. In an embodiment, the column does not comprise a filtering means at the base of the column.

The bed may be present in a suitable receptacle—such as a column. In the present context the term "column" relates to any kind of container which can be supplied with at least one inlet for the input of a mixture to the column and at least one outlet for the subsequent eluting of a particle of interest or protein of interest from the mixture. In one embodiment, the receptacle is column shaped. Typically expanded bed adsorption columns operate under plug flow conditions with minimal back-mixing and turbulence in the adsorbent bed. In accordance with the present invention the mixture is introduced into an expanded bed column comprising an adsorbent wherein the constituents of the mixture contact and interact with the adsorbents in the column. A person skilled in the art will be capable of designing a column with a certain diameter and height depending on the input volume of the mixture.

As the mixture is introduced into the column, the solid particulates and cell debris move freely around the adsorbents and eventually exit through the top of the column. As with any chromatographic step, the adsorbent typically undergoes strenuous washing to limit nonspecific interactions. Meanwhile, the particles of interest and proteins of interest will interact with the adsorbents, bind the adsorbents, and be retained on the column. The column may then be allowed to pack, the flow is reversed, and the particle of interest can be eluted from the beads as in traditional methods.

A further aspect relates to an expanded bed of adsorbent comprising a particle of interest reversibly bound thereto. The adsorbent suitably has one or more of the properties described herein for the adsorbent. A further aspect relates to the use of an expanded bed adsorbent or the use of EBA chromatography for capturing a particle of interest from a mixture.

The process for the capture of particles of interest from a mixture is based on adsorption to any type of solid phase material of any shape and format that can be used in EBA. Furthermore, the adsorption may be characterized by the use of selective adsorbent characteristics, ligand chemistry, or a combination thereof enabling the specific binding and subsequent elution of substantially only the particle of interest or alternatively enabling a group specific binding of a few biomolecular substances followed by selective and consecutive elution of the particle of interest from the adsorbent.

In various embodiments, the adsorbent is in the form of beads. The beads may be uniform in size, density, weight or a combination thereof or they may be variable in size, density, weight, or a combination thereof. One embodiment relates to beads that are uniform in size but have variable densities or weights, or both. This arrangement may create a distribution of beads. The size of the beads will typically range from 5 µm to 500 µm. Suitable sizes of beads may be in the diameter range of about 5 µm to 500 µm, such as about 5 µm to 400 µm, or about 5 µm to 300 µm, or about 5 µm to 200 µm, about 5 µm to 100 µm, about 50 µm to 400 µm, or about 50 µm to 300 µm, or about 50 µm to 200 µm, or about 50 µm to 150 µm or 50 µm to 100 µm—such as about 20 µm to 80 µm, about 150 µm, about 100 µm, or about 50 µm. At least about 70%, about 80%, about 90%, about 95%, about 98%, about 97%, about 98%, about 99% or 100% by volume of the individual beads may have this volume. The larger beads populate the lower portion of the fluidized bed while the smaller beads populate the upper portions. If the beads are too small, expansion will occur at velocities comparable to the escape velocity of the particulate contaminants, lowering capture efficiency. Likewise, if the beads are too large, fluidization requires higher flow rates and protein binding is impaired because of improper diffusion among the beads. The beads can be of any shape, such as but not limited to essentially spherical, elongated, cylindrical, columnar, or irregularly formed. In one embodiment, the beads are spherical. The skilled person in this field can choose the suitable bead size, shape, and porosity depending on the process to be used.

In another embodiment, the size of the beads that capture the particle of interest is between about 25 µm to 125 µm; suitably about 25 µm to 100 µm; more suitably about 25 µm to 95 µm; even more suitably about 25 µm to 90 µm; particularly suitably about 30 µm to 90 µm; more particularly suitably about 30 µm to 85 µm; even more particularly suitably about 35 µm to 85 µm; more suitably about 35 µm to 80 µm; more suitably about 40 µm to 80 µm; more suitably about 40 µm to 75 µm; more suitably about 45 µm to 75 µm; more suitably about 45 µm to 70 µm; more suitably about 40 µm to 70 µm; more suitably about 40 µm to 65 µm; more suitably about 45 µm to 65 µm; more suitably about 45 µm to 60 µm; more suitably about 45 µm to 55 µm; most suitably about 50 µm.

In another embodiment, the size of the beads that capture material other than the particle of interest, for example, plant materials, is between about 130 µm to 250 µm; suitably about 135 μm to 250 μm; more suitably about 135 μm to 225 μm; more suitably about 135 μm to 200 μm; more suitably about 135 μm to 175 μm; more suitably about 135 μm to 170 μm; more suitably about 140 μm to 170 μm; more suitably about 140 μm to 165 μm; more suitably about 140 μm to 160 μm; more suitably about 145 μm to 160 μm; more suitably about 145 μm to 145 μm; most suitably about 150 μm. Suitably, these beads may be used in a pre-capture step using an expanded bed adsorbent.

In another embodiment, the density of the adsorbent particle may be in the range of about 1 g/ml to 20 g/ml; more suitably in the range from about 2 g/ml to 20 g/ml; more suitably in the range from about 3 g/ml to 20 g/ml; more suitably in the range from about 4 g/ml to 20 g/ml; more suitably in the range from about 4 g/ml to 20 g/ml; more suitably in the range from about 5 g/ml to 20 g/ml; more suitably in the range from about 6 g/ml to 20 g/ml; more suitably in the range from about 7 g/ml to 20 g/ml; more suitably in the range from about 8 g/ml to 20 g/ml; more suitably in the range from about 9 g/ml to 20 g/ml; more suitably in the range from about 10 g/ml to 20 g/ml; more suitably in the range from about 11 g/ml to 20 g/ml; more suitably in the range from about 12 g/ml to 20 g/ml; more suitably in the range from about 13 g/ml to 20 g/ml; more suitably in the range from about 14 g/ml to 20 g/ml; more suitably in the range from about 14 g/ml to 19 g/ml; more suitably in the range from about 14 g/ml to 18 g/ml; more suitably in the range from about 14 g/ml to 17 g/ml; more suitably in the range from about 15 g/ml to 17 g/ml; most suitably 16 g/ml.

The present invention is not limited to any particular material for use as the adsorbent, and those having ordinary skill in the art will be able to select appropriate materials. The methods can use novel combinations of different beads or novel combinations of functional groups or ligands on the same bead. The beads can be, but are not limited to, very porous, macroporous, slightly porous, nonporous, hydrophilic, hydrophobic, highly charged, slightly charged, no charge, rigid, or swellable. The beads can be, but are not limited to, plastics, methacrylate, polysaccharides (such as agarose and cellulose), silica (for example, controlled pore glass), poly(styrenedivinyl)benzene, polyacrylamide, ceramic beads and derivatives of any of these. Further examples include, strong anion exchangers with high binding capacity, low binding capacity (for example, Q), weak anion exchange beads (for example, diethylaminoethyl (DEAE), ANX), strong cation exchange materials (for example, SP), or weak cation exchange materials (for example, CM).

To accentuate the difference between the velocities of adsorbents and particulates in the feedstock in the upward flow, many different adsorbent materials can be used. In order to process highly viscous feedstock or to achieve high flow rate, an increase in size, density, or both is desirable. In various embodiments of the invention, an increase in density can be accomplished by using a high density porous material or by coating a high density non-porous material with a material that is porous. Beads made only of organic material have limited density and would need to have very large diameters for conventional chromatography considerations such as high sedimentation velocity. Such large bead diameters result in long diffusional path lengths, which cause considerable mass transfer resistance, counteracting productivity. The present invention contemplates the use of composite beads that comprise an inert core material that is denser than the organic materials. In the present context the term "core" relates to the non-porous core which is present inside the beads. The core is not limited to being located in the centre of the bead. Such beads have the benefit of having a high density and a bead size suitable for the methods of the invention. The density of the materials can range from about 1.2 to about 4.0, for example, quartz (1.2), silica (1.4-1.6), Nd—Fe—B alloy (1.8-2.1), stainless steel, tungsten carbide (2.5-3.5), zirconium oxide (3.2), or zirconia (3.85). The porous material that can be used to coat the core includes but is not limited to, agarose, ceramic hydroxyapatite, cellulose, zirconium oxide gel, silica gel, and hydroxyethylmethacrylate-ethylene dimethylacrylate copolymer. Further examples of suitable non-porous core materials are inorganic compounds, metals, heavy metals, elementary non-metals, metal oxides, non-metal oxides, metal salts and metal alloys. Examples of such core materials are metal silicates, metal borosilicates; ceramics including titanium diboride, titanium carbide, zirconium diboride, zirconium carbide, tungsten carbide, silicon carbide, aluminum nitride, silicon nitride, titanium nitride, yttrium oxide, silicon metal powder, and molybdenum disilicide; metal oxides and sulfides, including magnesium, aluminum, titanium, vanadium, chromium, zirconium, hafnium, manganese, iron, cobalt, nickel, copper and silver oxide; non-metal oxides; metal salts, including barium sulfate; metallic elements, including tungsten, zirconium, titanium, hafnium, vanadium, chromium, manganese, iron, cobalt, nickel, indium, copper, silver, gold, palladium, platinum, ruthenium, osmium, rhodium and iridium, and alloys of metallic elements, such as alloys formed between said metallic elements, for example, stainless steel; crystalline and amorphous forms of carbon, including graphite, carbon black and charcoal. Suitable non-porous core materials are tungsten carbide, tungsten, steel and titanium beads—such as stainless steel beads. The non-porous core constitutes typically of at most 70% of the total volume of the adsorbent particle, such as at most 60%, suitably at most 50%, suitably at most 40%, suitably at most 30%, suitably at most 20%, suitably at most 15%, suitably at most 10% and most suitably at most 5%.

A commonly used material for use as the adsorbent is agarose, a material proven to work well for industrial scale chromatography. Thus, in one embodiment, the adsorbent is agarose or agarose-based. The macroporous structure of the (preferably highly cross-linked) agarose matrices combines good binding capacities for large molecules, such as proteins, with high chemical and mechanical stability. In another embodiment, the adsorbent is dextran or dextran-based. High mechanical stability is an important property of a matrix to be used to reduce the effects of attrition when beads are moving freely. Because the design of the expanded bed methods allows for considerations different from column chromatography, the agarose beads may be smaller or larger or different in amount of cross-linking from standard beads. These changes or no changes are contemplated for all structural materials in the bed materials. Modified agarose matrices may be less brittle than inorganic material such as some glass or ceramic materials.

Bead polydispersity within the column is contemplated by the present invention. The size and density gradients position the beads at specific locations with the column or bed. The smaller, lighter beads move to one position and the larger, heavier beads to a different one. Polydispersity or diversity in other bead characteristics is contemplated by the present invention. Size, density, binding capabilities, exclusion pore sizes, support material differences are a few of the wide variety of combinations of components and factors that are used in the methods of the invention.

In certain embodiments of the invention, the adsorbent comprises a ligand suitable for capturing particles of interest.

In certain embodiments of the invention, the adsorbent comprises a ligand suitable for purifying a particle of interest or a protein of interest.

Ligands that may be of use in the present invention include, but are not limited to: ligands that comprise, consist or consist essentially of: (i) benzylamine or a derivative thereof; (ii) an alkylamine, including an alkylamine having an alkyl group having 1-12 carbon atoms which may be straight or branched or cyclic, such as for example, methyl, ethyl, propyl, isopropyl, butyl, isobutyl, tert-butyl, pentyl, hexyl, heptyl, octyl, nonyl, decyl, undecyl, dodecyl, cyclopentyl, cyclohexyl or decalinyl, said alkyl group optionally being substituted with at least one group other than an acidic group; (iii) an alkenylamine, including an alkenyl group including a mono-, di- or polyunsaturated alkyl group with 2-12 carbon atoms which may be straight, branched or cyclic and in which the double bond(s) may be present anywhere in the chain or the ring(s), said alkenyl group optionally being substituted with at least one group other than an acidic group; (iv) an alkynylamine, including a $C_{2-12}$alkynyl group defined essentially as for the alkenylamine, including an alkynyl group that may be substituted with at least one group other than an acidic group; (v) an alkoxyamine with an $C_{2-12}$ alkoxy group that is optionally substituted with at least one group other than an acidic group; and (vi) an amine of mono- or bicyclic aromatic or heteroaromatic moieties, optionally substituted with at least one group other than an acidic group.

In a further embodiment, the ligand that is capable of capturing a particle of interest—such as a VLP—is selected from the group consisting of a ligand that comprises, consists or consist essentially of (i) benzylamine or a derivative thereof; (ii) an alkylamine, including an alkylamine having an alkyl group having 1-12 carbon atoms which may be straight or branched or cyclic, such as for example, methyl, ethyl, propyl, isopropyl, butyl, isobutyl, tert-butyl, pentyl, hexyl, heptyl, octyl, nonyl, dodecyl, cyclopentyl, cyclohexyl or decalinyl, said alkyl group optionally being substituted with at least one group other than an acidic group; (iii) an alkenylamine, including an alkenyl group including a mono-, di- or polyunsaturated alkyl group with 2-12 carbon atoms which may be straight, branched or cyclic and in which the double bond(s) may be present anywhere in the chain or the ring(s), said alkenyl group optionally being substituted with at least one group other than an acidic group; (iv) an alkynylamine, including a $C_{2-12}$alkynyl group defined essentially as for the alkenylamine, including an alkynyl group that may be substituted with at least one group other than an acidic group; (v) an alkoxyamine with an $C_{2-12}$ alkoxy group that is optionally substituted with at least one group other than an acidic group; and (vi) an amine of mono- or bicyclic aromatic or heteroaromatic moieties, optionally substituted with at least one group other than an acidic group or a combination thereof.

In a further embodiment, the ligand comprises, consists or consists essentially of an aromatic or heteroaromatic acid selected from the group consisting of carboxylic acids, sulfonic acids, phosphonic acids, and boronic acids. Suitably, the ligand is selected from the group consisting of 2-mercaptobenzoic acid, 2-mercaptonicotinic acid, 2-aminobenzoic acid, 3-aminobenzoic acid, and 4-aminobenzoic acid, 4-hydroxyphenyl-mercapto-acetic acid, 4-hydroxyphenyl-mercapto-propionic acid, 4-hydroxyphenyl-mercapto-butanoic acid, 2,3-dihydroxy-benzoic acid, 2,4 dihydroxy-benzoic acid, 2,5 di-hydroxy-benzoic acid, 2,6 dihydroxy-benzoic acid, 3,4-dihydroxy-benzoic acid, 3,5-dihydroxy-benzoic acid, mercaptobenzimidazole sulfonic acid, orthanilic acid, metanilic acid, sulphanilic acid, 4-methylaniline-2-sulphonic acid, 4-methoxyaniline-2-sulphonic acid, aniline-2,5-disulphonic acid, N-methylmetanilic acid, 7-amino-1-naphthol-3-sulphonic acid, 1-naphthol-4-sulphonic acid, 2-naphthol-6-sulphonic acid and 2-hydroxy-3-naphthoic acid, and 2-mercaptobenzimidazole-sulphonic acid.

In a further embodiment, the ligand comprises, consists or consists essentially of aromatic or heteroaromatic groups (radicals) selected from the groups consisting of i) ligands comprising the following types of functional groups: benzoic acids such as 2-aminobenzoic acids, 3-aminobenzoic acids, 4-aminobenzoic acids, 2-mercaptobenzoic acids, 4-amino-2-chlorobenzoic acids, 2-amino-5-chlorobenzoic acids, 2-amino-4-chlorobenzoic acids, 4-aminosalicylic acids, 5-aminosalicylic acids, 3,4-diaminobenzoic acids, 3,5-diaminobenzoic acids, 5-aminoisophthalic acids, and 4-aminophthalic acids; cinnamic acids such as hydroxy-cinnamic acids; nicotinic acids such as 2-mercaptonicotinic acids; naphthoic acids such as 2-hydroxy-1-naphthoic acid; quinolines such as 2-mercaptoquinoline; tetrazolacetic acids such as 5-mercapto-1-tetrazolacetic acid; thiadiazols such as 2-mercapto-5-methyl-1,3,4-thiadiazol; benzimidazols such as 2-amino-benzimidazol, 2-mercaptobenzimidazol, and 2-mercapto-5-nitrobenzimidazol; benzothiazols such as 2-aminobenzothiazol, 2-amino-6-nitrobenzothiazol, 2-mercaptobenzothiazol and 2-mercapto-6-ethoxybenzothiazol; benzoxazols such as 2-mercaptobenzoxazol; thiophenols such as thiophenol and 2-aminothiophenol; 2-(4-aminophenylthio)acetic acid; aromatic or heteroaromatic sulfonic acids and phosphonic acids, such as 1-amino-2-naphthol-4-sulfonic acid and phenols such as 2-amino-4-nitro-phenol; ii) ligands comprising 2-hydroxy-cinnamic acids, 3-hydroxy-cinnamic acid and 4-hydroxy-cinnamic acid; iii) ligands comprising a carboxylic acid and an amino group as substituents such as 2-amino-nicotinic acid, 2-mercapto-nicotinic acid, 6-amino-nicotinic acid and 2-amino-4-hydroxypyrimidine-carboxylic acid; iv) ligands comprising radicals derived from a benzene ring fused with a heteroaromatic ring system, for example, a ligand selected from benzimidazoles such as 2-mercapto-benzimidazol and 2-mercapto-5-nitro-benzimidazol; benzothiazols such as 2-amino-6-nitrobenzothiazol, 2-mercaptobenzothiazol and 2-mercapto-6-ethoxybenzothiazol; benzoxazols such as 2-mercaptobenzoxazol; and v) ligands chosen from the group of thiophenols such as thiophenol and 2-aminothiophenol.

The ligand may have an affinity for the particle of interest or the protein of interest. Accordingly, the ligand may be capable of a highly specific biological interaction such as that which may occur between an antigen and antibody, enzyme and substrate, or receptor and receptor ligand. Accordingly, the ligand may be an antibody, an antigen, an enzyme, an enzyme substrate, a receptor, a receptor ligand or an aptamer and the like. In one embodiment, the ligand is an antibody. The biological ligands may be used alone or in combination with one or more of the chemical ligands described herein. The biological ligand may comprise one or more of the same or different ligands optionally in combination with one or more of the chemical ligands as described herein.

The adsorbent comprising the ligand is typically equilibrated to the pH conditions at which the binding of the particle of interest optimally occurs. The equilibration step is typically carried out by applying a buffer at a pH in the range of about 3-10 such as in the range of about 5-7, suitably pH 7.

The beads which comprise the ligands will commonly comprise a plurality of ligands. In a specific embodiment, the beads comprise a ligand as described above in combination with a second kind of ligand, wherein the ligand according to the invention is present to at least about 30%, suitably at least about 50%, more suitably at least about 70% and most suitably at least about 90% of the total ligand amount. Such a combined ligand separation matrix may be designed for a specific case, where an element of further interactions improves its separation properties. The second kind of ligand may comprise one or more charged groups, such as a cation exchanger used to elute compounds by charge repulsion; hydrophobic groups; groups capable of hydrogen-bonding; affinity groups or the like. Thus, combinations of different ligands as described herein that are able to bind particles of interest are also contemplated, which may be present in equal ratios or different ratios.

In various embodiments, it is desirable to operate the methods at a flow rate that exceeds the terminal velocity of the particulates in the feedstock but not that of the beads. In one embodiment, the linear flow rate in the expanded bed is at least about 2 cm/min, at least about 3 cm/min, at least about 4 cm/min, at least about 5 cm/min, at least about 6 cm/min, at least about 7 cm/min, at least about 8 cm/min, at least about 10 cm/min, at least about 12 cm/min, at least about 15 cm/min, at least about 20 cm/min, at least about 25 cm/min, at least about 30 cm/min, at least about 40 cm/min, or at least about 50 cm/min. In another embodiment, the linear flow rate is in the range of about 1 cm/min to 15 cm/min, such as about 2 cm/min to 10 cm/min, or about 2 cm/min to 9 cm/min, or about 2 cm/min to 8 cm/min, or about 3 cm/min to 8 cm/min or about 3.5 cm/min to 7.5 cm/min. In one embodiment, the flow rate is about 3.8 cm/min. In another embodiment, the flow rate is about 7.5 cm/min. The flow rate can be measured by collecting a volume of liquid at the outlet in a defined period of time.

In other embodiments, the input of the feedstock in the expanded bed may be performed with a linear flow rate of at least about 150 cm/hour—such as at least about 180 cm/hour, at least about 200 cm/hour, at least about 210 cm/hour, at least about 220 cm/hour, at least about 230 cm/hour, at least about 240 cm/hour, at least about 250 cm/hour, at least about 300 cm/hour, at least about 400 cm/hour, at least about 425 cm/hour, at least about 450 cm/hour, at least about 475 cm/hour, at least about 500 cm/hour, or at least about 600 cm/hour. In another embodiment, the input of the feedstock in the expanded bed may be performed with a linear flow rate of about 200 to 500 cm/hour—such as about 300 to 500 cm/hour, or about 400 cm/hour. In one embodiment, the flow rate is about 228 cm/hour. In another embodiment, the flow rate is about 450 cm/hour.

The degree of expansion of the bed may be measured using the equation: height0/height1, where height1 is the height of the bed in packed bed mode without flow through the column and height0 is the height of the bed in expanded mode with a flow through the column. In one embodiment, the degree of expansion is in the range of 1 to 5, for example, 1 to 4 or 1 to 3 or 1 to 2—such as 1.1, 1.2, 1.3, 1.4, 1.5, 1.6, 1.7, 1.8 or 1.9. For some embodiments, the degree of expansion is at most about 1.2. In another embodiment, the flow-rate is about 5 cm/min and the degree of expansion is 1 to 2—such as 1.1, 1.2, 1.3, 1.4, 1.5, 1.6, 1.7, 1.8 or 1.9; suitably 1.2. In another embodiment, the flow-rate is about 6 cm/min and the degree of expansion is 1 to 2—such as 1.1, 1.2, 1.3, 1.4, 1.5, 1.6, 1.7, 1.8 or 1.9; suitably 1.2. In another embodiment, the flow-rate is about 7 cm/min and the degree of expansion is 1 to 2—such as 1.1, 1.2, 1.3, 1.4, 1.5, 1.6, 1.7, 1.8 or 1.9; suitably 1.2. In another embodiment, the flow-rate is about 8 cm/min and the degree of expansion is 1 to 2—such as 1.1, 1.2, 1.3, 1.4, 1.5, 1.6, 1.7, 1.8 or 1.9; suitably 1.2. In another embodiment, the flow-rate is about 9 cm/min and the degree of expansion is 1 to 2—such as 1.1, 1.2, 1.3, 1.4, 1.5, 1.6, 1.7, 1.8 or 1.9; suitably 1.2. In another embodiment, the flow-rate is about 10 cm/min and the degree of expansion is 1 to 2—such as 1.1, 1.2, 1.3, 1.4, 1.5, 1.6, 1.7, 1.8 or 1.9; suitably 1.2. In another embodiment, the flow-rate is about 4 cm/min (for example, about 3.8 cm/min) and the degree of expansion is 1 to 2—such as 1.1, 1.2, 1.3, 1.4, 1.5, 1.6, 1.7, 1.8 or 1.9; suitably 1.2. In another embodiment, the flow-rate is about 8 cm/min (for example, about 7.8 cm/min) and the degree of expansion is 1 to 2—such as 1.1, 1.2, 1.3, 1.4, 1.5, 1.6, 1.7, 1.8 or 1.9; suitably 1.2.

The use of an expanded bed adsorbent coupled with a ligand for the capture of a particle of interest from a mixture may comprise the steps of first providing a mixture comprising one or more particles of interest. The mixture may have a defined pH or the pH of the mixture may be adjusted to obtain a desired pH. The mixture is contacted with an expanded bed adsorbent and optionally washed with one or more buffers. One or more particles of interest may become reversibly bound to the adsorbent or they may remain unbound. The adsorbent may then be washed with a buffer to obtain a fraction comprising non-bound material. The adsorbent may then be washed with at least one elution buffer to obtain at least one eluate comprising one or more particles of interest that were reversibly bound to the adsorbent. The washing step, the elution step, or both may be performed with buffers that have a higher pH than the pH of the mixture that is initially contacted with the adsorbent. The buffer(s) may comprise one or more further compounds—such as one or more detergents. The adsorbent may be washed with a buffer between each elution step. The fraction comprising non-bound material or the particles of interest or both obtained in the elution step may be subjected to further downstream processing as discussed herein including, without limitation, chromatography, immunopurification, filtration, microfiltration, centrifugation, decantation, sedimentation and the like, or a combination of two or more of the foregoing techniques.

The degree of expansion of the bed during the elution step is in the range of 0.5 to 5, for example, 1 to 4 or 1 to 3 or 1 to 2—such as 1.1, 1.2, 1.3, 1.4, 1.5, 1.6, 1.7, 1.8 or 1.9. For some embodiments, the degree of expansion is at most about 1.2.

In one embodiment, two or more particles of interest may be captured from the mixture by using two or more different adsorbents, wherein one or more, for example all, of the adsorbents are in expanded bed mode. Accordingly, the present invention contemplates the use of two or more, three or more, four or more or five or more different adsorbents for the capture of particles of interest.

In a further aspect, the invention relates to a method of capturing a particle of interest from a mixture, the method comprising contacting the mixture with an expanded bed adsorbent under conditions where the particle of interest binds to the adsorbent, and changing the conditions such that the particle of interest is eluted from the adsorbent. In embodiments, the method captures at least 50% of the total amount of particles of interest initially present in the mixture, including at least 60%, 70%, 80% or 90% of the particles of interest. Even higher capture rates may be achieved—such as at least 92.5%, 95%, 96%, 97%, 98% or at least 99%.

Further embodiments of the present invention are now described. Prior to capture, host cells comprising the particles of interest may be lysed, homogenised, ground, pulverized, crushed, dried (for example, freeze dried), extruded or subjected to a combination of two or more of the foregoing. Other known methods which reduce the size of the bulk material, disrupt the cell(s), or release the contents of the cell(s), can also be used. If the host cell is a plant host cell then the cells may be disrupted or homogenized using methods known in the art—such as but not limited to a screw press (for example, a Vincent CP-4 screw press at about 15 kg/hr-20 kg/hr using at least 45-psi pressure on the cone), a pasta cutter, or one or more machines commonly used in tobacco processing (e.g., an extruder). The extract that is obtained is collected, and optionally stored. It is also referred to as green juice or green extract when green leaves are predominant in the starting material. Such extract comprises not only the content in the intercellular spaces (i.e. apoplast) but also the intracellular content of the cells. In one embodiment, the extract may be further treated by the addition of one or more chemicals or compositions and the like. Thus, in one embodiment, sodium metabisulfite may be added to the extract. This is an optional step since the particle of interest may be secreted from a cell.

The conductivity of the extract may be measured using methods known in the art—such as via the use of a Condutimeter Multi 350i/set. If the conductivity is not in the desired range then the extract may be diluted with deionized water before use. For example, it has been observed that homogenization of tobacco stems and leaves results in plant material that has a conductivity of about 20 mS/cm. This value has consistently been observed in homogenized plant materials derived from N. tabacum and N. bentamiana. According to one embodiment, conductivity should be in the range of 1 mS/cm to 10 mS/cm; suitably 2 mS/cm to 8 mS/cm; suitably 3 mS/cm to 7 mS/cm; suitably 4 mS/cm to 6 mS/cm, for example, 5.1, 5.2, 5.3, 5.4, 5.5, 5.6, 5.7, 5.8 or 5.9 mS/cm. According to another embodiment, conductivity should be in the range of 1 mS/cm to 5 mS/cm; suitably 2 mS/cm to 3 mS/cm, for example, 2.1, 2.2, 2.3, 2.4, 2.5, 2.6, 2.7, 2.8 or 2.9 mS/cm. In another embodiment, the pH of the extract is between about pH 6.0 to 8.0; suitably about pH 7.0.

It may be desirable to pre-treat the feedstock prior to capture. In the case where the particles of interest are present in a plant extract, it may be advantageous to remove some of the plant-derived macromolecules that can cause clogging and blockage during the capture process. According to one embodiment, an ion exchanger—such as a polyethylenimine (PEI) ion exchanger is used to bind the undesirable plant-derived macromolecules. This step can be carried out in batch incubation mode; suitably in a first column and the eluted material obtained therefrom is optionally contacted with a second column comprising an expanded bed. Suitably, the ion exchanger used in this pre-capture step has a mean adsorbent particle size of about 100 µm to 200 µm; suitably about 150 µm at about pH 7. Typically, the ion exchanger will be equilibrated with a suitable buffer—such as 0.5 M Tris/HCl buffer pH 7, followed by 10 mM Tris/HCl buffer pH 7.0. Other pre-capture steps are contemplated which may include filtration, microfiltration, centrifugation (for example, slow speed centrifugation), decantation or sedimentation or a combination of two or more of these methods.

According to another embodiment, the pre-capture step comprises the use of an expanded bed of adsorbent. Suitably, the size of the beads used in the pre-capture step is between about 130 µm to 250 µm; suitably about 135 µm to 250 µm; more suitably about 135 µm to 225 µm; more suitably about 135 µm to 200 µm; more suitably about 135 µm to 175 µm; more suitably about 135 µm to 170 µm; more suitably about 140 µm to 170 µm; more suitably about 140 µm to 165 µm; more suitably about 140 µm to 160 µm; more suitably about 145 µm to 160 µm; more suitably about 145 µm to 145 µm; most suitably about 150 µm. Suitably, these beads may be used in a pre-capture step using an expanded bed adsorbent. Accordingly, a further aspect of the invention relates to a method for capturing a particle of interest from a mixture comprising the steps of: (a) providing a first expanded bed of adsorbent; (b) contacting the mixture with the first adsorbent under conditions such that unwanted materials in the mixture binds to the first adsorbent; (c) providing a second expanded bed of adsorbent; (d) contacting the particle of interest from step (b) with the second adsorbent under conditions such that the particles of interest bind to the second adsorbent; (e) optionally washing the second adsorbent; (f) optionally eluting the particle of interest from the second adsorbent; and (g) optionally repeating steps (a) to (f) one or more further times.

In one embodiment, the adsorbent used in the expanded bed mode is an anion exchange resin—such as a diethylaminoethyl cellulose-based ion exchange resin, suitably a diethylaminoethyl cellulose dextran-based ion exchange resin. The resin will typically be equilibrated with buffer to a pH of between about pH 6.0 to 8.0; suitably pH 7.0 using, for example, 0.5 M Tris/HCl buffer pH7, followed by 10 mM Tris/HCl pH 7.0. In one embodiment, the mean adsorbent particle size of the adsorbent is between about 25 µm to 200 µm; suitably about 25 µm to 75 µm and most suitably about 50 µm. If the method is carried out in an expanded bed column, then the skilled person will appreciate that various sizes of columns can be used. In one embodiment, the column is 1 cm in diameter with a column height of about 70 cm and a bed height of about 15 cm. This use of larger columns—such as columns that can be used on an industrial scale—is also encompassed by the present invention. For example, columns may range in size from about 1 cm in diameter to at least 1500 cm in diameter—such as up to about 10 cm in diameter, up to about 100 cm in diameter, up to about 250 cm in diameter, up to about 500 cm in diameter, up to about 750 cm in diameter, up to about 1000 cm in diameter, up to about 1250 cm in diameter, up to about 1500 cm in diameter, up to about 1750 cm in diameter or at least up to about 2000 cm in diameter. Other diameters include 2 cm diameter, 10 cm diameter, 45 cm diameter and 150 cm diameter. The supernatant is loaded onto the column at a desired flow rate, as described herein and after loading the column is typically washed with washing buffer with a pH of between about pH 6.0 to 8.0; suitably pH 7.0—such as 10 mM Tris/HCl pH 7.0. Bound material may then be eluted using a suitable elution buffer, which will typically be at a higher or lower pH to the wash buffer. In one embodiment, the wash buffer comprises 50 mM Tris/HCl and 1 M NaCl, pH 9.0. Suitably, the eluate is collected in one fraction and the pH is adjusted during elution to pH 7 by adding a buffer—such as 1 M Tris/HCl, pH 6.5 solution to the tube before collecting the eluate.

According to one mode of operation, the binding and elution of a particle of interest present in a plant extract is achieved using a DEAE ion exchanger following a pre-capture with a PEI ion exchanger.

In another embodiment, the extract is not pre-treated such that a particle of interest can be isolated in a one step binding and elution process. This mode of operation is particularly suitable for the large scale capture of particles of interest using expanded bed adsorption. Thus, extracts of at least 100 liters (for example, at least 250 liters, at least 500 liters, at least 750 liters, at least 1000 liters, at least 1250 liters, at least 1500 liters, at least 1750 liters, and at least 2000 liters) can be processed according to this method.

In one embodiment, the bead composition is agarose based—such as epichlorohydrin cross-linked agarose (for example, at 4% w/v). The bead may comprise a core of different composition to the rest of the bead—such as a tungsten carbide core. A suitable ligand is a DEAE ion exchanger typically with a mean diameter of about 50 µm. The average density of the adsorbent particle is suitably about 16 kg/L. A suitable column diameter is about 45 cm with a void volume in sedimented status comprising approximately 40% of the packed volume. In one embodiment, the column is equilibrated with 0.5 M Tris-Cl buffer, pH7 followed by 10 mM Tris-Cl buffer, pH7. Suitably, the loading of the extract is achieved by pumping upward the extract at a flow rate as described herein. The expansion factor is typically in the region of 2.0-2.5 and unbound material is washed out with 10 mM Tris/HCl, pH7 at the same expansion rate. Following the EBA chromatography step, the particles of interest may be eluted with 50 mM Tris-Cl and 1M NaCl, pH9 at an expansion rate of about 1.2. Eluted fractions may be neutralized by adding 1M Tris/HCl, pH 6.5 to the container before collecting the elution peak. Fractions containing or comprising particles of interest may be pooled for further capture and purification.

The average density of the beads may be about 1 g/ml to 20 g/ml, the linear flow rate may be at least about 150 cm/hour, the degree of expansion of the expanded bed may be from about 1 to 5.

In an embodiment of the present invention the adsorbent may optionally be washed or equilibrated or both, with one or more washing buffers and equilibration buffers, respectively. The mixture applied to the adsorbent may be a conditioned mixture. In the case where the adsorbent is not held within a column it may be a solid phase, such as for membrane based adsorption, for example, a membrane filter, fibers or sheets, whereto the ligand is coupled.

Accordingly, a further aspect relates to a method for capturing a particle of interest from a mixture comprising the steps of: (i) providing an expanded bed of adsorbent comprising a ligand in a column at a settled bed height of above 10 cm, wherein the density of the adsorbent is between about 1 g/ml to 20 g/ml, wherein the degree of expansion of the expanded bed is between about 1 to 5 and wherein the average size of the adsorbent particle is between about 25 μm to about 200 μm; (ii) equilibrating the resin material at a pH in the range of about pH 6.0 to 8.0; (iii) providing a mixture comprising a particle of interest, wherein said mixture has a conductivity of between about 1 mS/cm to 10 mS/cm; (iv) loading the mixture onto the column at a linear flow rate in the range of between about 1 cm/min to 15 cm/min to bind the particle of interest; (iv) washing the loaded column using a buffer having a pH in the range of about pH 6.0 to 8.0; and (v) eluting the bound particle of interest from the column in one or more fractions.

As referred to herein, a "buffer" is a solution that resists changes in pH by the addition of acid or base by the action of its acid-base conjugate components. Various buffers can be employed depending on the desired pH of the buffer and the particular step in the capture process. Non-limiting examples of buffer components that can be used to desirably control the pH range for a method of the invention include acetate, citrate, histidine, phosphate, ammonium buffers such as ammonium acetate, succinate, MES, CHAPS, MOPS, MOPSO, HEPES, Tris, and the like, as well as combinations of these TRIS-malic acid-NaOH, maleate, chloroacetate, formate, benzoate, propionate, pyridine, piperazine, ADA, PIPES, ACES, BES, TES, tricine, bicine, TAPS, ethanolamine, CHES, CAPS, methylamine, piperidine, boric acid, carbonic acid, lactic acid, butaneandioic acid, diethylmalonic acid, glycylglycine, HEPPS, HEPPSO, imidazole, phenol, POPSO, succinate, TAPS, benzylamine, trimethyl- or dimethyl- or ethyl- or phenylamine, ethylenediamine, or morpholine. Additional components (additives) can be present in a buffer as needed, for example, salts can be used to adjust buffer ionic strength, such as sodium chloride, sodium sulfate and potassium chloride; and other additives such as amino acids (such as glycine and histidine), chaotropes (such as urea), alcohols (such as ethanol, mannitol, glycerol, and benzyl alcohol), detergents (see supra.), and sugars (such as sucrose, mannitol, maltose, trehalose, glucose, and fructose). The buffer components and additives, and the concentrations used, can vary according to the type of chromatography practiced in the invention.

The term "detergent" refers to ionic, zwitterionic and nonionic surfactants, which are useful for preventing aggregation of proteins and to prevent non-specific interaction or binding of contaminants to the protein of interest, and can be present in various buffers used in the present invention, including sanitization, equilibration, loading, post-load wash(es), elution or strip buffers. In particular embodiments, a detergent is added to a wash buffer. Examples of detergents that can be used in the invention include, but are not limited to, polysorbates (for example, polysorbates 20 or 80); poloxamers (for example, poloxamer 188); Triton; sodium dodecyl sulfate (SOS); sodium lauryl sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleylamidopropyl-, myristamidopropyl-, palmidopropyl-, or isostearamidopropyl-betaine (for example, lauroamidopropyl); myristamidopropyl-, palmidopropyl-, or isostearamidopropyl-dimethylamine; sodium methyl cocoyl-, or disodium methyl oleyl-taurate; MONAQUAT™ series (Mona Industries, Inc., Paterson, N.J.); Igepal CA-630, Pluronic, Triton, BRIJ, Atlas G2127, Genapol, HECAMEG, LUBROL PX, MEGA, NP, THESIT, TOPPS, CHAPS, CHAPSO, DDMAU, EMPIGEN BB, AWITTERGENT and C12E8. The detergent can be added in any working buffer and can also be included in the feed containing the molecule of interest. Detergents can be present in any amount suitable for use in the methods described herein, for example, from about 0.001% to about 20% and typically from about 0.01% to about 1%. In a particular embodiment, polysorbate 80 is used in a wash buffer for CEXC.

Chromatography performance may be monitored using various methods that are well known in the art—such as by measurement of UV absorption at 280 nm and 600 nm, by conductivity or by pH, or a combination thereof.

The capture of desired particles of interest may be monitored using an appropriate assay specific for the protein of interest. Assays—such as the well known Bradford assay may be used to determine the total protein content of fractions. SOS-PAGE may be used to establish purity. Western blotting may be used for the identification and characterization of the protein of interest. Methods for measuring protein activity can also be used—such as the hemagglutinin assay as described herein.

According to another embodiment, the expanded bed and column is cleaned and regenerated following use. Thus for example, after elution, the resin is cleaned and regenerated by washing with 0.5 M NaOH, followed by distilled water. Re-equilibration can be achieved using in 10 mM Tris-Cl buffer, pH7.

Accordingly, aspects of the present invention relate to the capture of a particle of interest from a plant. Thus, one aspect relates to a method for capturing a particle of interest from a plant, a plant cell or a plant extract comprising the use of an expanded bed or EBA chromatography. According to one embodiment, this method comprises the steps of: (a) providing an expanded bed of adsorbent; suitably a DEAE based adsorbent; (b) contacting the plant material with the adsorbent; (c) optionally rinsing the adsorbent; and (d) optionally eluting the particle of interest from the adsorbent. Suitably the conductivity of the plant extract prior to contact with the adsorbent is from 1 mS/cm to 10 mS/cm, suitably from 2 mS/cm to 3 mS/cm. Suitably the adsorbent comprises a plurality of beads—such as beads comprising agarose and a ligand suitable for binding a particle of interest. The beads may have a mean diameter of about 50 μm. Suitably the ligand comprises, consists or consists essentially of an anion exchange resin—such as a diethylaminoethyl cellulose-based ion exchange resin, suitably a diethylaminoethyl cellulose dextran-based ion exchange resin. Suitably the average density of the beads is from about 1 g/ml to 20 g/ml. Suitably the linear flow rate is at least about 150 cm/hour. Suitably the degree of expansion of the expanded bed is from about 1 to 5.

VLPs are generally antigenically similar to virions produced in an infection, but lack genetic information sufficient to replicate and thus are typically non-infectious. VLPs may be morphologically similar to virions produced in an infection but this is not always the case. VLPs—such as plant derived VLPs—may have a considerable size distribution and may be a different shape to the virions produced in an infection—such as less spherical, longer axis or have a squashed appearance. Thus, VLPs may sometimes be seen as deformed viruses which make the capture thereof challenging.

VLPs have been produced from components of a wide variety of virus families including Parvoviridae (for example, adeno-associated virus), Retroviridae (for example, HIV), and Flaviviridae (for example, Hepatitis C virus). VLPs can be produced in a variety of cell culture systems including mammalian cell lines, insect cell lines, yeast, and plant cells. In certain embodiments, one or more of the protein species present in a VLP may be modified from the naturally occurring sequence. VLPs may be produced in suitable host cells including mammalian cells, bacterial cells, plant cells and insect cells. In one embodiment, the VLPs are produced in cells of a plant. VLPs can often be produced in large quantities by heterologous expression. VLPs may be isolated from the host or host cell as intact structures. VLPs may be assessed for structure and size by, for example, immunoassay, functional assays (for example, aggluntination), electron microscopy, or by size exclusion chromatography.

VLPs may comprise one or more or two or more different proteins of interest. The proteins may be of different biological origins but at least one of which is of viral origin. For VLPs comprising more than one protein species, the protein species may be from the same species of virus, or may comprise a protein from a different species, genus, subfamily or family of virus. The VLPs may additionally comprise other types of molecules that are non-proteinaecous, such as but not limited to lipids and carbohydrates.

In one embodiment, the VLP is a multimeric assembly of monomeric units of a protein of interest. In various embodiments, the protein of interest is a viral protein, such as but not limited to a capsid. Most viral structures are based on the structure of their capsids, and can be present in helical, icosahedral or isometric, or enveloped forms. Helical symmetry has protein subunits arranged around the circumference of the virus, forming a disk. Icosahedrally symmetrical capsids form a quasi-spherical structure; and with enveloped viruses, protein subunits are exposed to the external environment. In various embodiments, a VLP comprises capsids, including from three to about 200 capsids. In one embodiment, the VLP includes at least 30, at least 50, at least 60, at least 90 or at least 120 capsids. In another embodiment, each VLP includes at least 150 capsids, at least 160, at least 170, or at least 180 capsids. In other embodiments, the protein of interest may be a viral matrix protein or a viral glycoprotein and the like.

In one embodiment, the VLP is expressed as an icosahedral structure. In another embodiment, the VLP is expressed in the same geometry as the native virus that the capsid sequence is derived from. In another embodiment, the VLP does not have the identical geometry of the native virus. In one embodiment, at least one of the capsids comprises at least one protein of interest.

In one embodiment, the VLP captured by the present invention can be used to make a pharmaceutical composition, including but not limited to a vaccine—such as an influenza or avian influenza vaccine. Such a vaccine can be administered to a human or animal to prevent an infection by a pathogen, such as but not limited to virus, bacteria, protozoan, nematode, parasite, or to treat an infection by such a pathogen.

The particle of interest may be a bacterial ghost particle. This type of particle is an empty bacterial cell envelope of a bacterium—such as a gram-negative bacterium. They are typically prepared by controlled heterologous expression of a gene which effects a partial lysis of the bacteria, particularly gram-negative bacteria. For example, the lytic gene may be the bacteriophage PhiX174 gene E encoding a polypeptide which is inserted into the cell envelope complex of gram-negative bacteria and leads to the formation of a transmembrane tunnel structure through the inner and outer membrane. The inner diameter of this tunnel structure may be in the range of about 20 nm-400 nm, particularly 40 nm-200 nm or 500 nm-1,000 nm depending on the lysis conditions applied. The cytoplasmic components are liberated by means of this tunnel structure, wherein an empty cell envelope complex having an intact morphology, a so-called bacterial ghost, is obtained. The use of bacterial ghosts is disclosed in WO91/13555 and WO93/01791. The bacterial ghost particle may be a recombinant ghost particle. The bacterial ghost particle may be a recombinant ghost particle displaying one or more proteins of interest—such as a vaccine antigen—on its surface.

The process may produce at least 0.1 g/L protein in the form of VLPs. In another embodiment, the process produces 0.1 g/L to 10 g/L protein in the form of VLPs. In other embodiments, the process produces at least about 0.2, 0.3, 0.4, 0.5, 0.6, 0.7, 0.8, 0.9 or 1.0 g/L protein in the form of VLPs. In one embodiment, the total amount of VLPs produced are at least 1.0 g/L.

A portion of the expressed viral capsid operably linked to a protein of interest may be formed in an insoluble aggregate in the cell. In one embodiment, the protein of interest is renatured from the insoluble aggregate as discussed herein.

In one embodiment, the protein operably linked to a viral capsid sequence comprises at least two amino acids. In another embodiment, the proteins comprise at least three, at least four, at least five, or at least six amino acids. In another embodiment, the proteins are at least seven, at least eight, at least nine, at least ten, or at least 11, 12, 13, 14, 15, 16, 17, 18, 19, 20, 30, 45, 50, 60, 70, 80, 90, 100, 200, 300, 400, 500, 600, 700, 800, 900 or 1000 or more amino acids long. In one embodiment, the protein has a molecular weight of at least 25 kDa, 50 kDa, 100 kDa or 150 kDa or more.

The protein of interest may be a heterologous protein that is not derived from the virus and, optionally, is not derived from the same species as the host cell.

The protein of interest may be a functional protein; a structural protein; an antigen; an immunogen; a toxin; an antimicrobial protein, a therapeutic protein or a prophylactic protein useful in the treatment or prevention or both of disease of humans or animals. Fragments, fusion proteins, precursors, or concatamers of the proteins described herein are also contemplated. Non-limiting examples of functional proteins include, but are not limited to, immunoactive proteins (for example, antigenic proteins, allergenic proteins, immunoregulators, immunomodulators); signaling and signal transduction proteins and inhibitory proteins (for example, toxic, biocidal, or biostatic proteins, such as proteins, toxins and antimicrobial proteins). Structural proteins include, but are not limited to, aptamers; folding proteins, adhesion-promoting proteins, interfacial proteins, microstructure and nanostructure-architectural proteins and pre-activation proteins. Catalytic proteins include, for example, RNA-editing proteins; catalytic proteins of tRNA synthetases; ribosome-inactivating proteins; and viral catalytic proteins. The protein of interest can be an epitope, a hapten, of a related protein (for example, antigenic viral proteins; virus related proteins, antibody idiotypic domains; cell surface proteins; antigenic proteins of human, animal, protist, plant, fungal, bacterial, or archaeal origin; allergenic proteins and allergen desensitizing proteins).

The protein may also be an immunoregulator or immunomodulator (for example, interferons, interleukins, immunodepressants and immunopotentiators); an antibody (for example, single chain antibodies; single chain antibody fragments and constructs, for example, single chain Fv molecules; antibody light chain molecules, antibody heavy chain molecules, domain-deleted antibody light or heavy chain molecules; single chain antibody domains and molecules, for example, a CH1, CH1-3, CH3, CH1-4, CH4, VHCH1, CL, CDR1, or FR1-CDR1-FR2 domain; paratopic peptides; microantibodies); another binding protein (for example, aptamers, intracellular and cell surface receptor proteins, receptor fragments).

The protein may be an enzyme substrate or an enzyme inhibitor or a cell surface receptor ligand, agonist, and antagonist, a hormone, a cytokine, chemokine, virokine, and viroceptor hormone releasing and release-inhibiting protein, a neurotransmitter or channel blocker, a toxin, or toxin precursor. The protein can also be a metabolism- and digestion-related protein, a cell adhesion modulating or mediating protein, extracellular matrix protein, a neuroprotectant or myelination-promoting protein; or an aggregation inhibitory protein. The protein of interest may be a secreted protein.

The coding sequence for the protein may be a native coding sequence but will more typically be a coding sequence that has been selected, improved, or optimized for use in the selected expression host cell, for example, by synthesizing the gene to reflect the codon use preference of a host species, or inclusion of a signal peptide.

In one embodiment, the protein of interest is an antigen that can be used in a vaccine or a vaccine composition. Suitably, the vaccine also comprises a pharmaceutically acceptable carrier or an adjuvant, or both. It is contemplated that vaccines are prophylactic or therapeutic. A "prophylactic" treatment is a treatment administered to a subject who does not exhibit signs of a disease or exhibits only early signs for the purpose of decreasing the risk of developing pathology. The vaccine may be given as a prophylactic treatment to reduce the likelihood of developing a pathology or to minimize the severity of the pathology, if developed. A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective.

In one embodiment, the antigen is hemagglutinin (HA) or a fragment or derivative thereof. HA is a viral surface glycoprotein comprising approximately 560 amino acids. It is responsible for adhesion of a virus and its penetration into a host cell in the early stages of infection. There are at least 16 known HA subtypes, categorized as an H1, H2, H3, H4, H5, H6, H7, H8, H9, H10, H11, H12, H13, H14, H15 or H16 subtype. Hemagglutinin is found on the surface of influenza viruses as well as many other bacteria and viruses. Currently, the most significant causes of influenza infections in humans are those attributable to subtypes H1N1 and H3N2 of influenza type A. However, influenza strains that may cause pandemic infection are, for instance, of the H5N1 subtype which are not protected against by typical influenza vaccines. H2, H7 and H9 subtypes also have pandemic potential. Highly pathogenic avian influenza viruses are capable of causing severe respiratory disease and mortality in birds. This feature is known only for HA of H5 and H7 subtypes. Because of the ability of some avian viruses to transmit to humans, they also become a human health concern. The pathogenicity of avian influenza viruses is a polygenic property but the HA protein has been shown to have the primary role in infection. The HA protein may be expressed in monomeric, dimeric or trimeric form. Any HA subtypes and variants, as well as the monomeric, dimeric or trimeric forms of any HA can be a protein of interest and be present in a VLP described herein.

Haemagglutinin protein may be detected by ELISA using standard methods which may comprise the use of antibodies. Methods for measuring the activity of haemagglutination are well known in the art and include incubation with red blood cells as described in WO2004/098533.

The host for the production of a particle of interest will typically be one in which the viral protein does not allow replication or infection of the cell. In one embodiment, the viral protein will be derived from a virus that does not infect the species of cell that the host cell is derived from. For example, in one embodiment, the viral species infects mammals and the expression system utilises a plant host cell. The host cell may be modified to improve the assembly of the particle of interest. The host cell may, for example, be modified to include chaperone proteins that promote the formation of particles of interest from expressed viral proteins. In another embodiment, the host cell is modified to include a repressor protein to more efficiently regulate the expression of the capsid to promote regulated formation of the particles of interest.

Host cells include bacterial, yeast, algal, insect, mammalian and plant cells.

In some embodiments of the invention, the bacterial host cell is of the *Agrobacterium* genus, for example, *A. radiobacter, A. rhizogenes*, and *A. rubi*. In some embodiments of the invention the bacterial host cell is of the *Arthrobacter* genus, for example, *A. aurescens, A. citreus, A. globformis, A. hydrocarboglutamicus, A. mysorens, A. nicotianae, A. paraffineus, A. protophonniae, A. roseoparqffinus, A. sulfureus*, and *A. ureafaciens*. In some embodiments of the invention the bacterial host cell is of the *Bacillus* genus, for example, *B. thuringiensis, B. anthracia, B. megaterium, B. subtilis, B. lentos, B. circulans, B. pumilus, B. lautus, B. coagulans, B. brevis, B. firmus, B. alkaophius, B. licheniformis, B. clausii, B. stearothermophilus, B. halodurans* and *B. amyloliquefaciens*. In particular embodiments, the host cell will be an industrial *Bacillus* strain including but not limited to *B. subtilis, B. pumilus, B. licheniformis B. megaterium, B. clausii, B. stearothermophilus* and *B. amyloliquefaciens*. In some embodiments the bacterial host cell is of the *Clostridium* genus, for example, *C. acetobutylicum, C. tetani* E88, *C. lituseburense, C. saccharobutylicum, C. perfringens*, and *C. beijerinckii*. In some embodiments the bacterial host cell is of the *Corynebacterium* genus for example, *C. glutamicum* and *C. acetoacidophilum*. In some embodiments the bacterial host cell is of the *Escherichia* genus, for example, *E. coli*. In some embodiments the bacterial host cell is of the *Erwinia* genus, for example, *E. uredovora, E. carotovora, E. ananas,*

*E. herbicola*, *E. punctata*, and *E. terreus*. In some embodiments the bacterial host cell is of the *Pantoea* genus, for example, *P. citrea*, and *P. agglomerans*. In some embodiments the bacterial host cell is of the *Pseudomonas* genus, for example, *P. putida*, *P. aeruginosa* and *P. mevalonii*. In some embodiments the bacterial host cell is of the *Streptococcus* genus, for example, *S. equisimiles*, *S. pyogenes*, and *S. uberis*. In some embodiments the bacterial host cell is of the *Streptomyces* genus, for example, *S. ambofaciens*, *S. achromogenes*, *S. avermitilis*, *S. coelicolor*, *S. aureofaciens*, *S. aureus*, *S. fungicidicus*, *S. griseus*, and *S. lividans*. In some embodiments the bacterial host cell is of the *Zymomonas* genus, for example, *Z. mobilis*, and *Z. lipolytica*. Because of the potential of fast, efficient, inexpensive, and abundant yields of recombinant proteins, bacteria have been examined as host cells in expression systems for the production of particles of interest—such as VLPs. Researchers have shown that particular wild-type viral capsids without recombinant protein inserts can be transgenically expressed in non-tropic enterobacteria. Researchers have also shown that these capsids can be assembled, both in vivo and in vitro, to form particles of interest—such as VLPs.

A yeast host cell may be a cell of a genus of, but not limited to *Candida*, *Hansenula*, *Saccharomyces*, *Schizosaccharomyces*, *Pichia*, *Kluyveromyces*, and *Yarrowia*. In some embodiments of the invention, the yeast cell is *Hansenula polymorphs*, *Saccharomyces cerevisiae*, *Saccaromyces carlsbergensis*, *Saccharomyces diastaticus*, *Saccharomyces norbensis*, *Saccharomyces kluyveri*, *Schizosaccharomyces pombe*, *Pichia pastoris*, *Pichia finlandica*, *Pichia trehalophila*, *Pichia kodamae*, *Pichia membranaefaciens*, *Pichia opuntiae*, *Pichia thermotolerans*, *Pichia salictaria*, *Pichia quercuum*, *Pichia pijperi*, *Pichia stipitis*, *Pichia methanolica*, *Pichia angusta*, *Kluyveromyces lactis*, *Candida albicans*, and *Yarrowia lipolytica*.

A fungal host cell may be a cell of a genus of, but not limited to *Achlya*, *Acremonium*, *Aspergillus*, *Aureobasidium*, *Bjerkandera*, *Ceriporiopsis*, *Cephalosporium*, *Chrysosporium*, *Cochliobolus*, *Corynascus*, *Cryphonectria*, *Cryptococcus*, *Coprinus*, *Coriolus*, *Diplodia*, *Endothis*, *Fusarium*, *Gibberella*, *Gliocladium*, *Humicola*, *Hypocrea*, *Myceliophthora*, *Mucor*, *Neurospora*, *Penicillium*, *Podospora*, *Phlebia*, *Piromyces*, *Pyricularia*, *Rhizomucor*; *Rhizopus*, *Schizophyllum*, *Scytalidium*, *Sporotrichum*, *Talaromyces*, *Thermoascus*, *Thielavia*, *Trametes*, *Tolypocladium*, *Trichoderma*, *Verticillium*, *Volvariella*, or teleomorphs, or anamorphs, and synonyms or taxonomic equivalents thereof.

In some embodiments on the invention, the host cell is an algal cell such as, *Chlamydomonas* (for example, *C. Reinhardtii*) and *Phormidium* (*P.* sp. ATCC29409).

Examples of insect host cells include a *Lepidoptora* cell line, such as *Spodoptera frugiperda* (Sf9 or Sf21) or *Trichoplusioani* cells (High Five).

Examples of mammalian host cells include Chinese hamster ovary (CHO) cell lines, (for example CHO-K1; ATCC CCL-61), Green Monkey cell lines (COS) (for example COS 1 (ATCC CRL-1650), COS 7 (ATCC CRL-1651)); mouse cells (for example NS/O), Baby Hamster Kidney (BHK) cell lines (for example ATCC CRL-1632 or ATCC CCL-10), and human cells (for example HEK 293 (ATCC CRL-1573)).

In one embodiment, the host is a plant, and the host cell is a plant cell. The plant cell may be derived or derivable from a plant or it may be a cultured plant cell that is cultured outside of a plant. Thus, in one embodiment, the plant is a plant cell—such as a plant cell grown in culture or outside of a plant such as an in vitro grown plant cell or clumps of cells. Non-limiting examples of plants include monocots and dicots, such as crop plants, ornamental plants, and non-domesticated or wild plants. Further examples include plants of commercial or agricultural interest, such as crop plants (especially crop plants used for human food or animal feed), wood- or pulp-producing trees, vegetable plants, fruit plants, and ornamental plants.

Non-limiting examples of plants include grain crop plants (such as wheat, oat, barley, maize, rye, triticale, rice, millet, sorghum, quinoa, amaranth, and buckwheat); forage crop plants (such as forage grasses and forage dicots including alfalfa, vetch, clover, and the like); oilseed crop plants (such as cotton, safflower, sunflower, soybean, canola, rapeseed, flax, peanuts, and oil palm); tree nuts (such as walnut, cashew, hazelnut, pecan, almond, and the like); sugarcane, coconut, date palm, olive, sugarbeet, tea, and coffee; wood- or pulp-producing trees; vegetable crop plants such as legumes (for example, beans, peas, lentils, alfalfa, peanut), lettuce, asparagus, artichoke, celery, carrot, radish, the brassicas (for example, cabbages, kales, mustards, and other leafy brassicas, broccoli, cauliflower, Brussels sprouts, turnip, kohlrabi), cucurbits (for example, cucumbers, melons, summer squashes, winter squashes), alliums (for example, onions, garlic, leeks, shallots, chives), members of the Solanaceae (for example, tomatoes, eggplants, potatoes, peppers, groundcherries), and members of the Chenopodiaceae (for example, beet, chard, spinach, quinoa, amaranth); fruit crop plants such as apple, pear, citrus fruits (for example, orange, lime, lemon, grapefruit, and others), stone fruits (for example, apricot, peach, plum, nectarine), banana, pineapple, grape, kiwifruit, papaya, avocado, and berries; and ornamental plants including ornamental flowering plants, ornamental trees and shrubs, ornamental groundcovers, and ornamental grasses. Further examples of dicot plants include, but are not limited to, canola, cotton, potato, quinoa, amaranth, buckwheat, safflower, soybean, sugarbeet, and sunflower, more suitably soybean, canola, and cotton. Further examples of monocots include, but are not limited to, wheat, oat, barley, maize, rye, triticale, rice, ornamental and forage grasses, sorghum, millet, and sugarcane. Plants as recombinant protein production hosts contain a unique set of contaminants that may be removed during capture and purification of the particles of interest. Furthermore, plant solids, which require early removal after extraction, are generally in higher concentration, wider in size range, and denser than traditional bacterial and mammalian cell culture debris. A typical plant processing and purification scheme consists of isolation of the plant tissue containing the recombinant protein, fractionation of the tissue along with particle size reduction, extraction of the target protein into an aqueous medium, clarification of the crude extract, and finally purification of the product. An improvement in the capture of particles of interest from plant cells will therefore favorably impact the overall production cost.

Plant material that is suitable for use in the present invention may be or may be derived from a monocotyledonous or dicotyledonous plant or a plant cell system, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genera *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phieum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*.

Suitable species may include Panicum spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cordgrass), *Medicago sativa* (alfalfa), *Arundo donax* (giant reed), *Secale cereale* (rye), *Salix* spp. (willow), *Eucalyptus* spp. (eucalyptus), *Triticosecale* (triticum—wheat×rye), bamboo, *Helianthus annuus* (sunflower), *Carthamus tinctorius* (safflower), *Jatropha curcas* (Jatropha), *Ricinus communis* (castor), *Elaeis guineensis* (palm), *Linum usitatissimum* (flax), *Brassica juncea, Beta vulgaris* (sugarbeet), *Manihot esculenta* (cassava), *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Rosa* spp. (rose), *Dianthus caryophyllus* (carnation), *Petunia* app. (petunia), *Poinsettia pulcherrima* (poinsettia), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum* pretense (timothy), *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica* napes (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

The plant material may be or may be derived from naturally occurring, mutant, non-naturally occurring or transgenic tobacco plants, including plants of the genus *Nicotiana*, various species of *Nicotiana*, including *N. benthamiana* and *N. tabacum* (for example, LA B21, LN KY171, TI 1406, Basma, Galpao, Perique, Beinhart 1000-1, and Petico). Other species include *N. acaulis, N. acuminate, N. acuminate* var. *multiflora, N. africana, N. alata, N. amplexicaulis, N. arentsii, N. attenuata, N. benavidesii, N. rustica, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longflora, N. maritime, N. megalosiphon, N. miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondli, N. repanda, N. rosulata, N. rosulata* subsp. *ingulba, N. rotundifolia, N. setchellii, N. simulans, N. solanifolia, N. spegazzinii, N. stocktonii, N. suaveolens, N. sylvestris, N. tabacum. N. thyrsiflora, N. tomentosa, N. tomentosiformis, N. trigonophylla, N. umbratica, N. undulate, N. velutina, N. wigandioides*, and *N. x sanderae*.

The use of plant material that is from or is derived from cultivars or elite cultivars is also contemplated. Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, Denzizli, DF911, Galpao tobacco, GL 26H, GL 350, GL 600, GL 737, GL 939, GL 973, HB 04P, K 149, K 326, K 346, K 358, K394, K 399, K 730, KDH 959, KT 200, KT204LC, KY10, KY14, KY 160, KY 17, KY 171, KY 907, KY907LC, KTY14xL8 LC, Karabaglar, Little Crittenden, McNair 373, McNair 944, msKY 14xL8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, Turkish Samson, VA 309, VA359, DAC, Mata, Fina, PO2, BY-64, AS44, RG17, RG8, HBO4P, Basma Xanthi BX 2A, Coker 319, Hicks, McNair 944 (MN 944), Burley 21, K149, Yaka JB 125/3, Kasturi Mawar, NC 297, Coker 371 Gold, PO2, Wislica, Simmaba, Turkish Samsun, AA37-1, B13P, F4 from the cross BU21× Hoja Parado line 97, Samsun or PO1. Non-limiting examples of *N. tabacum* cultivars are AA 37-1, B 13P, Xanthi (Mitchell-Mor), KTRD#3 Hybrid 107, Bel-W3, 79-615, Samsun Holmes NN, KTRDC#2 Hybrid 49, KTRDC#4 Hybrid 110, Burley 21, BY-64, KTRDC#5 KY 160 SI, KTRDC#7 FCA, KTRDC#6 TN 86 SI, Coker 371 Gold, K 149, K 326, K 346, K 358, K 394, K 399, K 730, KY 10, KY 14, KY 160, KY 17, KY 8959, KY 9, KY 907, MD 609, McNair 373, NC 2000, PG 01, PG 04, M066, PO1, PO2, PO3, RG 11, RG 17, RG 8, Speight G-28, TN 86, TN 90, VA 509, AS44, Banket A1, Basma Drama B84/31, Basma I Zichna ZP4/B, Basma Xanthi BX 2A, Batek, Besuki Jember, C104, Coker 319, Coker 347, Criollo Misionero, DAC Mata Fina, Delcrest, Djebel 81, DVH 405, Galpão Comum, HBO4P, Hicks Broadleaf, Kabakulak Elassona, Kasturi Mawar, Kutsage F1, KY 14xL8, KY 171, LA BU 21, McNair 944, NC 2326, NC 71, NC 297, NC 3, PVH 03, PVH 09, PVH 19, PVH 2110, Red Russian, Samsun, Saplak, Simmaba, Talgar 28, Turkish Samsun, Wislica, Yayaldag, NC 4, TR Madole, Prilep HC-72, Prilep P23, Prilep PB 156/1, Prilep P12-2/1, Yaka JK-48, Yaka JB 125/3, TI-1068, KDH-960, TI-1070, TW136, Samsun NN, Izmir, Basma, TKF 4028, L8, TKF 2002, TN90, GR141, Basma xanthi, GR149, GR153, Petit Havana or Xanthi NN.

A transient expression system is particularly suitable for generating plants that are used in the methods of the invention. Such a transient expression system, suitably used with various species of *Nicotiana* and varieties of *N. tabacum*, involves the infiltration of a suspension of genetically engineered *Agrobacterium tumefaciens* into leaves of whole plants through a physical method known in the art (e.g., application of vacuum, or pressure greater than atmospheric pressure) and relying on the ability of *Agrobacterium* to transfer nucleic acid molecules encoding the protein of interest into the plant cells, typically an expression construct that can replicate in *Agrobacterium*. The copy number of the expression construct in an infiltrated plant cell is higher than that used to generate a transgenic plant. Transient expression that is used to generate plants used in the invention is characterized by not requiring integration of the expression construct into the plant genome, although infiltration of *Agrobacterium* may result in integration. Thus, the majority of the infiltrated plant cells do not comprise a genome that contains an integrated expression construct. Nor does transient expression require transmission of the expression construct into a progeny plant. Generally, within 2 to 15 days or suitably 4 to 6 days after infiltration, recombinant protein accumulates in the infiltrated plant cells and forms virus-like particles. The biomass, particularly infiltrated leaves, can at this time be harvested and processed for isolation of the particles. Accordingly, the plant material may be derived from a plant (such as a variety of *Nicotiana benthamiana* or *Nicotiana tabacum*) that is transiently expressing a protein that is present in the virus-like particles, suitably a plant that is infiltrated with *Agrobacterium* cells comprising an expression construct that encodes the protein and enables the expression of the protein transiently in an infiltrated plant cell.

Use of plant materials as feedstock poses additional challenges because of the high solids content, for example, greater than 5%, 10%, 11%, 12%, 13%, 14%, 15%, 16%, 17%, 18%, 19% or 20% w/w. The feedstock may contain a high concentration of material that is larger than those found in cell culture supernatant, for example, particles of interest in the ranges of 10E-4 to 10E-2, 10E-4 to 10E-1, 10E-3 to 10E-1, 10E-4 tot mm, 10E-3 to 1 mm, or 10E-2 to 1 mm. The feedstock is chemically complex containing typically lipids, starches, lignins, phenolic compounds, and pigments. The low yield of recombinant protein in plant relative to cell culture requires loading of higher volumes of feedstock.

If the mixture is or is derived from a plant then it may be in the form of a plant juice extract. As used herein, the term "plant juice extract" refers to a liquid material derived from a plant that comprises chlorophyll. The plant juice extract may be a conditioned plant juice extract.

Whilst the skilled person will understand that the protein of interest may be contained in one or more particles of interest, for some embodiments, it may be desirable to isolate or purify the protein of interest from the particles of interest. Accordingly, the methods described herein may comprise an optional further step of purifying the protein from the particles of interest. Thus the protein of interest that is contained in the particles of interest may be purified to substantial purity by standard techniques well known in the art, including, but not limited to, ammonium sulfate or ethanol precipitation, acid extraction, anion or cation exchange chromatography, phosphocellulose chromatography, hydrophobic interaction chromatography, affinity chromatography, nickel chromatography, hydroxylapatite chromatography, reverse phase chromatography, lectin chromatography, preparative electrophoresis, detergent solubilization, selective precipitation with such substances as column chromatography, immunopurification methods, and others. For example, proteins having established molecular adhesion properties can be reversibly fused a ligand. With the appropriate ligand, the protein can be selectively adsorbed to a purification column and then freed from the column in a relatively pure form. In addition, protein can be purified using immunoaffinity columns or Ni-NTA columns.

It also to be understood that the methods of the invention may comprise further steps of processing the material either before or after contact with the expanded bed. Accordingly, the methods described herein may include further upstream or downstream processing steps. Thus, in one embodiment, the method comprises an optional further step of treating the material prior to or after contact with the expanded bed. In another embodiment, the method comprises an optional further step of treating the particle of interest once it has been eluted from the adsorbent. Thus, by way of example the material may be subjected to ammonium sulfate or ethanol precipitation, acid extraction, anion or cation exchange chromatography, phosphocellulose chromatography, hydrophobic interaction chromatography, affinity chromatography, nickel chromatography, hydroxyapatite chromatography, reverse phase chromatography, lectin chromatography, preparative electrophoresis, detergent solubilization, selective precipitation with such substances as column chromatography, immunopurification methods, filtration, microfiltration, centrifugation, decantation, or sedimentation, or a combination of the foregoing.

A "cation exchange resin" is negatively charged, and which has free cations for exchange with cations in an aqueous solution passed over or through the adsorbent or solid phase. Any negatively charged ligand suitable to form the cation exchange resin can be used, for example, a carboxylate, sulfonate and others as described below. Commercially available cation exchange resins include, but are not limited to, for example, those having a sulfonate based group (for example, MonoS, MiniS, Source 15S and 30S, SP Sepharose Fast Flow™, SP Sepharose High Performance from GE Healthcare, Toyopearl SP-650S and SP-650M from Tosoh, Macro-Prep High S from BioRad, Ceramic HyperD S, Trisacryl M and LS SP and Spherodex LS SP from Pall Technologies); a sulfoethyl based group (for example, Fractogel SE, from EMD, Poros S-10 and S-20 from Applied Biosystems); a sulphopropyl based group (for example, TSK Gel SP 5PW and SP-5PW-HR from Tosoh, Poros HS-20 and HS 50 from Applied Biosystems); a sulfoisobutyl based group (for example, (Fractogel EMD $SO_3$ from EMD); a sulfoxyethyl based group (for example, SE52, SE53 and Express-Ion S from Whatman), a carboxymethyl based group (for example, CM Sepharose Fast Flow from GE Healthcare, Hydrocell C M from Biochrom Labs Inc., Macro-Prep CM from BioRad, Ceramic HyperD CM, Trisacryl M CM, Trisacryl LS CM, from Pall Technologies, Matrx Cellufine C500 and C200 from Millipore, CM52, CM32, CM23 and Express-Ion C from Whatman, Toyopearl CM-650S, CM-650M and CM-650C from Tosoh); sulfonic and carboxylic acid based groups (for example BAKEPVBOND Carboxy-Sulfon from J. T. Baker); a carboxylic acid based group (for example, WP CBX from J. T. Baker, DOWEX MAC-3 from Dow Liquid Separations, Amberlite Weak Cation Exchangers, DOWEX Weak Cation Exchanger, and Diaion Weak Cation Exchangers from Sigma-Aldrich and Fractogel EMD COO—from EMD); a sulfonic acid based group (e.g., Hydrocell SP from Biochrom Labs Inc., DOWEX Fine Mesh Strong Acid Cation Resin from Dow Liquid Separations, UNOsphere S, WP Sulfonic from J. T. Baker, Sartobind S membrane from Sartorius, Amberlite Strong Cation Exchangers, DOWEX Strong. Cation and Diaion Strong Cation Exchanger from Sigma-Aldrich); and an orthophosphate based group (for example, PI 1 from Whatman).

An "anion exchange resin" is positively charged, thus having one or more positively charged ligands attached thereto. Any positively charged ligand attached to the adsorbent or solid phase suitable to form the anionic exchange resin can be used, such as quaternary amino groups. Commercially available anion exchange resins include DEAE cellulose, Poros PI 20, PI 50, HQ 10, HQ 20, HQ 50, D 50 from Applied Biosystems, Sartobind Q from Sartorius, MonoQ, MiniQ, Source 15Q and 300, Q, DEAE and ANX Sepharose Fast Flow, Q Sepharose high Performance, QAE SEPHADEX™ and FAST Q SEPHAROSE™ (GE Healthcare), WP PEI, WP DEAM, WP QUAT from J. T. Baker, Hydrocell DEAE and Hydrocell QA from Biochrom Labs Inc., UNOsphere Q, Macro-Prep DEAE and Macro-Prep High Q from Biorad, Ceramic HyperD Q, ceramic HyperD DEAE, Trisacryl M and LS DEAE, Spherodex LS DEAE, QMA Spherosil LS, QMA Spherosil M and Mustang Q from Pall Technologies, DOWEX Fine Mesh Strong Base Type I and Type II Anion Resins and DOWEX MONOSPHER E 77, weak base anion from Dow Liquid Separations, Intercept Q membrane, Matrex Cellufine A200, A500, Q500, and 0800, from Millipore, Fractogel EMD TMAE, Fractogel EMD DEAE and Fractogel EMD DMAE from EMD, Amberiite weak strong anion exchangers type I and II, DOWEX weak and strong anion exchangers type I and II, Diaion weak and strong anion exchangers type I and II, Duolite from Sigma-Aldrich, TSK gel and DEAE 5PW and 5PW-HR, Toyopearl SuperQ-650S, 650M and 650C, QAE-550C and 650S, DEAE-650M and 650C from Tosoh, QA52, DE23, DE32, DE51, DE52, DE53, Express-Ion D and Express-Ion Q from Whatman.

The use of thiophilic chromatography is also contemplated and is also known as thiophilic adsorption chromatography. The term "thiophilic" refers to the selectivity that proteins have for sulfone groups that lie in close proximity to thioether groups. This is a type of non-affinity chromatography in which a protein of interest, which contains thiophilic regions and aromatic amino residues, binds to a sulphur containing ligand for the isolation of the protein. A thiophilic gel can be prepared by reducing divinylsulfone (coupled to Sepharose 4B) with β-mercaptoethanol. Thiophilic adsorption chromatography is based on electron donor-acceptor properties and is distinct from chromatography based on hydrophobicity. Hydrophobic associations and ionic interactions do not occur with thiophilic sorbents since thio-ethylsulfone structures do not possess pronounced hydrophobicity or ionic charges. Examples of commercially available thiophilic chromatography resins include Fractogel EMD TA (Merck; Rahway, N.J.), Uniflow and Superflow resin (Clontech) and T-Gel (Pierce).

The term "affinity chromatography" refers to a separation technique in which a protein of interest is reversibly and specifically bound to a biologically specific ligand, usually as a combination of spatial complementarity and one or more types of chemical interactions, e.g., electrostatic forces, hydrogen bonding, hydrophobic forces, and van der Waals forces at the binding site. These interactions are not due to the general properties of the molecule such as isoelectric point, hydrophobicity or size but are a result of specific interactions between the protein of interest and the ligand, e.g., immunoglobulin binding to an epitope, protein A binding to immunoglobulin, interactions between a biological response modifier and its cell surface receptor. In many instances, the biologically specific ligand is also a protein or a polypeptide and can be immobilized onto a solid phase, such as the bead.

A "mixed mode ion exchange resin is also contemplated herein and refers to a solid phase which is covalently modified with cationic, anionic or hydrophobic moieties. Examples of mixed mode ion exchange resins include BAKERBOND ABX™ (J. T. Baker; Phillipsburg, N.J.), ceramic hydroxyapatite type 1 and II and fluoride hydroxyapatite (BioRad; Hercules, Calif.) and MEP and MBI HyperCel (Pall Corporation; East Hills, N.Y.).

The term "hydrophobic charge induction chromatography" (or "HCIC") is a type of mixed mode chromatographic process in which the protein of interest in the mixture binds to an ionizable ligand through mild hydrophobic interactions in the absence of added salts (e.g., a lyotropic salt). The mixed mode refers to one mode for binding and another mode for elution. For example, a solid phase useful in HCFC contains a ligand which has the combined properties of thiophilic effect (i.e., utilizing the properties of thiophilic chromatography), hydrophobicity and an ionizable group for its separation capability. Accordingly, an adsorbent used in a method of the invention contains a ligand that is ionizable and mildly hydrophobic at neutral (physiological) or slightly acidic pH, e.g., about pH 5 to 10, preferably about pH 6 to 9.5. At this pH range, the ligand is predominantly uncharged and binds a protein of interest via mild non-specific hydrophobic interaction. As pH is reduced, the ligand acquires charge and hydrophobic binding is disrupted by electrostatic charge repulsion towards the solute due to the pH shift. Examples of suitable ligands for use in HCIC include any ionizable aromatic or heterocyclic structure (e.g. those having a pyridine structure, such as 2-aminomethylpyridine, 3-aminomethylpyridine and 4-aminomethylpyridine, 2-mercaptopyridine, 4-mercaptopyridine or 4-mercaptoethylpyridine), mercaptoacids, mercaptoalcohols, mercaptomethylimidazole, 2-mercaptobenzimidazole, aminomethylbenzimidazole, histamine, mercaptobenzimidazole, diethylaminopropylamine, aminopropylmorpholine, aminopropylimidazole, aminocaproic acid, nitrohydroxybenzoic acid, nitrotyrosine/ethanolamine, dichlorosalicylic acid, dibromotyramine, chlorohydroxyphenylacetic acid, hydroxyphenylacetic acid, tyramine, thiophenol, glutathione, bisulphate, and dyes, including derivatives thereof.

The one or more proteins expressed in the particle of interest can have a specific activity of at least 20%, 30%, or 40%, and suitably at least 50%, 60%, or 70%, and most suitably at least 80%, 90%, or 95% of that of the native protein that the sequence is derived from. Further, the substrate specificity ($k_{cat}/K_m$) is optionally substantially similar to that of the native protein. Typically, $k_{cat}/K_m$ will be at least 30%, 40%, or 50% of that of the native protein; and more suitably at least 60%, 70%, 80%, or 90%. Methods of assaying and quantifying measures of protein and protein activity and substrate specificity ($k_{cat}/K_m$) are well known to those of skill in the art.

The activity of the recombinant protein can be compared with a previously established native protein standard activity. Alternatively, the activity of the recombinant protein can be determined in a simultaneous, or substantially simultaneous, comparative assay with the native protein. For example, an in vitro assay can be used to determine any detectable interaction between a recombinant protein and a target, for example between an expressed enzyme and substrate, between expressed hormone and hormone receptor, between expressed antibody and antigen, etc. Such detection can include the measurement of calorimetric changes, proliferation changes, cell death, cell repelling, changes in radioactivity, changes in solubility, changes in molecular weight as measured by gel electrophoresis or gel exclusion methods, phosphorylation abilities, antibody specificity assays such as ELISA assays, etc. In addition, in vivo assays include, but are not limited to, assays to detect physiological effects of the produced protein in comparison to physiological effects of the native protein, for example induction of an immune response, or inflammation. Generally, any in vitro or in vivo assay can be used to determine the active nature of the particle of interest. Alternatively, the proteins produced in the present invention can be assayed for the ability to stimulate or inhibit interaction between the protein and a molecule that normally interacts with the protein, for example a substrate. Such assays can typically include the steps of combining the protein with a substrate molecule under conditions that allow them to interact, and detect the biochemical consequence of the interaction.

If the expressed protein is expressed as an insoluble protein then it can be renatured or refolded to generate secondary and tertiary protein structure conformation. Protein refolding steps can be used, as necessary, in completing configuration of the recombinant product. Refolding and renaturation can be accomplished using an agent that is known in the art to promote dissociation/association of proteins. For example, the protein can be incubated with dithiothreitol followed by incubation with oxidized glutathione disodium salt followed by incubation with a buffer containing a refolding agent such as urea.

Recombinant protein can also be renatured, for example, by dialyzing it against phosphate-buffered saline (PBS) or 50 mM Na-acetate, pH 6 buffer plus 200 mM NaCl. Alternatively, the protein can be refolded while immobilized on a column, such as the Ni NTA column by using a linear 6M-1M urea gradient in 500 mM NaCl, 20% glycerol, 20 mM Tris/HCl pH 7.4, containing protease inhibitors. The renaturation can be performed over a period of 1.5 hours or more. After renaturation the proteins can be eluted by the addition of 250 mM imidazole. Imidazole can be removed by a final dialyzing step against PBS or 50 mM sodium acetate pH 6 buffer plus 200 mM NaCl. The purified protein can be stored at 4° C. or frozen at −80° C.

Formulations of particles of interest having the desired degree of purity obtained or obtainable according to the present invention may be prepared for storage by mixing with optional pharmaceutically acceptable carriers, excipients or stabilizers (see Remington's Pharmaceutical Sciences 16th edition, Osol, A. Ed. (1980)) in the form of lyophilized formulations or aqueous solutions. Acceptable carriers, excipients, or stabilizers are nontoxic to recipients at the dosages and concentrations employed and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example Zn-protein complexes); or non-ionic surfactants such as TWEEN™, PLURONICS™ or polyethylene glycol (PEG).

The invention will be further described in the following examples, which are not intended to limit the scope of the invention described in the claims.

EXAMPLES

The following examples are provided as an illustration and not as a limitation. Unless otherwise indicated, the present invention employs conventional techniques and methods of biochemistry, molecular biology and plant biology.

Example 1

Transient expression of influenza virus-like particles in *Nicotiana benthamiana* Influenza virus-like particles are produced in *Nicotiana benthamiana* plants as described in D'Aoust, M.-A., Lavoie, P.-O., Couture, M. M.-J., Trépanier, S., Guay, J.-M., Dargis, M., Mongrand, S., Landry, N., Ward, B. J., Vézina, L.-P. Influenza virus-like particles produced by transient expression in *Nicotiana benthamiana* induce a protective immune response against a lethal viral challenge. Plant Biotechnology Journal 6 (2008) 930-940.

Example 2

Detection of Haemagglutinin

Haemagglutination is measured by incubation with red blood cells as described in WO2004/098533. Haemagglutinin protein is detected by ELISA using standard methods. For the detection of haemagglutinin H5 protein, a rabbit anti-H5 antibody from Immunetech (Catalog IT-003-005V) and a horseradish peroxidase-labelled secondary antibody from Jackson (Catalog 11-035-046) are used.

Example 3

Extraction of *N. benthamiana*

*N. benthamiana* plants infiltrated as described in Example 1 and by D'Aoust et al. (2008, supra) are incubated in the greenhouse for 6 days before harvesting. Upon harvesting of leaves, the biomass is kept overnight at 4° C. in the dark and homogenized using a screw press (Vincent CP-4) at 15-20 kg/hr using at least 45-psi pressure on the cone. The green juice extract is collected and sodium metabisulfite is added to the green juice to a final concentration of 10 mM. Conductivity is measured and where needed the extract is diluted with water before use in capture experiments.

Example 4

Ligands for Binding Virus-like Particles from Plant Juice Extracts

Extract. An *N. benthamiana* green juice extract containing haemagglutinin H5 virus-like particles (D'Aoust at al. (2008), supra) was obtained using a screw press as described in Example 3. The green juice extract was diluted 5-fold in deionized water, final pH 7 and conductivity was measured. Conductivity was 5.6 mS/cm. Four different ligands were tested for binding: a diethylaminoethyl (DEAE) ion exchanger, a dextran based DEAE ion exchanger, a dextran based chloromethyl-2-benzimidazol and a dextran based 1-(2-chloroethyl)piperidine hydrochloride ligand. The ratio of the various adsorbents to sample used was 1:5. After batch incubation in static mode, the supernatant was collected and haemagglutination was measured according to the procedure of Example 2.

Results. The amount of haemagglutinin as measured using a haemagglutination assay in the supernatant upon incubation with a DEAE, a dextran based DEAE, a dextran based chloromethyl-2-benzimidazol and a dextran based 1-(2-chloroethyl)piperidine hydrochloride ligand, as well as bound to the ligand, is given in Table 1. In this experiment virus-like particles comprising haemagglutinin, in a green plant juice extract, bound best to a DEAE-based ion exchanger adsorbent.

TABLE 1

Ratio of various adsorbents to green juice extract containing haemagglutinin virus-like particles, and haemagglutination activity (% of initial extract) of the supernatants and bound materials upon incubation of the extract with the various adsorbents in static mode.

| Ligand | Ratio | Haemagglutination (% of initial extract) | |
|---|---|---|---|
| | | Supernatant | Bound |
| DEAE | 1:5 | 13 | 87 |
| DEAE dextran based | 1:5 | 13 | 87 |
| Chloromethyl-2-benzimidazol dextran based | 1:5 | 67 | 33 |
| 1-(2-Chloroethyl) piperidine hydrochloride dextran based | 1:5 | 67 | 33 |

Example 5

Influence of Conductivity to Binding to a DEAE Ion Exchanger

The effect of the conductivity of a green juice extract containing haemagglutinin H5 virus-like particles as obtained according to the description in Examples 1 and 3 to the binding of the virus-like particles to a DEAE ligand in static binding mode was measured to investigate how high in conductivity a virus-like particle in a green juice extract can still bind a DEAE ion exchanger.

The DEAE ion exchanger was equilibrated with 5 bed volumes of 0.5 M Tris/HCl, pH 7 buffer, followed by 10 bed volumes of 2 mM NaCl, pH 7. A green juice extract was diluted 2.5, 3, 3.4, 4, 5, 6 and 7 times with deionized water and pH adjusted to 7. The conductivity of the various diluted green juice extracts was measured and the extracts were incubated for 2 h in static binding/batch mode with a DEAE ion-exchanger. The various conductivities are presented in Table 2. The ratio for each corresponded to 1:1 with undiluted extract. After batch incubation, supernatants were collected and haemagglutination was measured according to the method of Example 2. The results are represented in Table 2. In this experiment the binding of virus-like particles in a green juice extract was equally efficient at low and high conductivity and in highly and less diluted green juice extracts.

TABLE 2

Binding of haemagglutinin to a DEAE ion exchanger at different conductivities of a green juice extract in static mode.

| Dilution | Conductivity (mS/cm) | Haemagglutination (%) | |
|---|---|---|---|
| | | Supernatant | Bound |
| 7 | 3.52 | 9 | 91 |
| 6 | 4.51 | 9 | 91 |
| 5 | 5.47 | 9 | 91 |
| 4 | 6.34 | 9 | 91 |
| 3.4 | 7.04 | 9 | 91 |
| 3 | 8.31 | 9 | 91 |
| 2.5 | 9.41 | 9 | 91 |

Example 6

Two Step Capture Process for a Plant-derived Virus-like Particle

Two step process. The green plant juice extract obtained according to the method described in Example 3 utilises a pre-capture since the extract and especially any material in the extract causing the green colour sticks to most ligands and causes clogging and blockage of the column. To this end, a two step capture process for a plant-derived virus-like particle was set up. The process comprised:

Step 1, binding of impurities and materials determining the green colour of a green plant juice extract in static binding/batch incubation mode using a polyethyleneimine (PEI) ion exchanger with a mean particle size of 150 μm at pH 7;

Step 2, binding of the virus-like particles from the supernatant of Step 1 in expanded bed adsorption mode using a DEAE ion exchanger with a mean particle size of 50 μm at pH 7.

Experimental set-up. An N. benthamiana extract was prepared as described in Example 3 and was filtered and diluted 5-fold with deionized water before use. Final pH was 7 and total volume for incubation in Step 1 was 150 mL. Conductivity was 5.3 mS/cm. Equilibration of the PEI ion exchanger was with 5 bed volumes of 0.5 M Tris/HCl buffer pH 7, followed by 10 bed volumes of 10 mM Tris/HCl buffer pH 7.0. The ratio of the PEI adsorbent to green juice extract in static mode was 1:15. A total of 9.5 mL of PEI adsorbent was used. Incubation was for 30 min at room temperature and 140 mL of the supernatant was collected after incubation for Step 2. In Step 2, 120 mL supernatant of Step 1 was adjusted to pH 7.0 and run in expanded bed adsorption mode. Conductivity was 5.4 mS/cm and equilibration of the DEAE ion exchanger used in expanded bed mode was with 5 bed volumes of 0.5 M Tris/HCl buffer pH7, followed by 10 bed volumes of 10 mM Tris/HCl pH 7.0. A total of 12 of DEAE adsorbent was used. The expanded bed column was 1 cm in diameter with a column height of 70 cm. Bed height was 15 cm. The ratio of DEAE adsorbent to sample was 1:10. The supernatant of Step 1 was loaded onto the column at a flow rate of 3.8 cm/min and after loading the column was washed with washing buffer containing 10 mM Tris/HCl pH 7.0. Bound material was eluted using an elution buffer containing 50 mM Tris/HCl and 1 M NaCl, pH 9.0. Run through and wash fractions were collected at 25 mL. volumes. The eluate was collected in one fraction and the pH was adjusted during elution to pH 7 by adding ¹/₁₀ volume of a 1 M Tris/HCl, pH 6.5 solution to the tube before collecting the eluate.

Detection of haemagglutinin. The amount of haemagglutinin protein was estimated for the filtered N. benthamiana green juice extract prior to entering Step 1, the supernatant after incubation in static mode, the flow through, the wash and the eluate after expanded bed mode adsorption and elution, as described in Example 2. Total protein content in extracts and fractions was estimated using standard protocols.

Results. The amount of haemagglutinin as measured using a haemagglutination assay in filtered green juice extract, starting material for incubation in static mode with a PEI ion exchanger, the supernatant derived upon incubation of extract with the PEI ion exchanger, the starting material for expanded bed adsorption using a DEAE ion exchanger, the run through and eluate upon elution of the expanded bed column, are given in Table 3 together with the total protein content of said fractions and samples. In this experiment most of the materials causing the green colour and clogging of the column could be removed in Step 1 using the PEI adsorbent without loss of haemagglutinin protein and the virus-like particles comprising the haemagglutinin protein could be captured during expanded bed adsorption mode using a DEAE ion exchanger.

TABLE 3

Haemagglutination activity (% of initial extract) and total protein content (mg/mL) for the various extracts and fractions of Step 1 and 2.

| | Fraction | | | | | |
|---|---|---|---|---|---|---|
| Assay | Step 1 Diluted extract | Step 1 Start material PEI | Step 1 Super-natant after PEI | Step 2 Start material DEAE | Step 2 Run through + wash fractions | Step 2 Eluate from DEAE |
| Haemag-glutination (in %) | 100 | 100 | 100 | 100 | 0 | 67 |
| Total protein (in mg/mL) | 0.22 | 0.25 | 0.14 | 0.14 | ND | 0.06 |

ND, not determined.

Example 7

Optimization of Elution Conditions for a DEAE Ion Exchanger

Experimental set-up. The binding and elution of a virus-like particle present in a green plant juice extract obtained according to the method described in Example 3 with a DEAE ion exchanger in packed bed mode and following a pre-capture with a PEI ion exchanger as described in Example 6 was tested using an elution buffer containing 50 mM Tris/HCl, pH 8.5 to which was added 1 M NaCl, 0.8 M NaCl, 0.6 M NaCl, 0.4 M NaCl, 0.2 M NaCl or 0.1 M NaCl. Before loading of the extract, the green plant juice extract was diluted 5 times in deionized water and the pH was adjusted to pH 7. Conductivity was 5.1 mS/cm. The filtered green plant juice extract was first incubated with a PEI ion exchanger of mean particle size of 150 μm in batch incubation mode at a ratio of extract to ligand of 15:1 for 30 min as described in Step 1 of Example 6. The DEAE ion exchanger used had a mean particle size of 50 μm and the ratio of supernatant to adsorbent was 5:1. The amount of haemagglutinin protein was measured as described in Example 2. The relative amounts of haemagglutinin in run through and wash, bound to DEAE ion exchanger and eluate, are given in Table 4. In this experiment the use of an elution buffer containing 0.4, 0.6, 0.8 or 1.0 M NaCl resulted in similar capture of virus-like particles as measured using a haemagglutination assay.

TABLE 4

Relative haemagglutination activity in run through and wash, bound and eluate fractions using different elution buffers in packed bed mode using a DEAE ion exchanger.

| Elution buffer 50 mM Tris/ | Relative haemagglutination activity (%) | | |
|---|---|---|---|
| HCl, pH 8.5 plus | Run through and wash | Bound | Eluate |
| 1M NaCl | 0 | 100 | 67 |
| 0.8M NaCl | 0 | 100 | 67 |
| 0.6M NaCl | 0 | 100 | 67 |

TABLE 4-continued

Relative haemagglutination activity in run through and wash, bound and eluate fractions using different elution buffers in packed bed mode using a DEAE ion exchanger.

| Elution buffer 50 mM Tris/ | Relative haemagglutination activity (%) | | |
|---|---|---|---|
| HCl, pH 8.5 plus | Run through and wash | Bound | Eluate |
| 0.4M NaCl | 0 | 100 | 67 |
| 0.2M NaCl | 0 | 100 | 45 |
| 0.1M NaCl | 0 | 100 | 9 |

Example 8

Break Through Curve in Expanded Bed Adsorption Mode at Different Flow Rates

The binding of a virus-like particle present in a green plant juice extract and obtained according to the method described in Example 3 was measured at a flow rate of 228 cm/h and 450 cm/h in a one step binding process in expanded bed adsorption mode. A DEAE ion exchanger was used which was equilibrated using 5 bed volumes of 0.5 M Tris/HCl buffer pH 7 and 10 bed volumes of 10 mM Tris, pH 7. The DEAE ion exchanger used had a mean particle size of 50 μm. The ratio of adsorbent to green plant juice extract was always 1:20. Bed height was 50 cm and the column contained 39.3 mL of adsorbent DEAE ion exchanger. Green plant juice extracts were diluted 5 times in deionized water and conductivity was measured before loading. Washing buffer was 10 mM Tris, pH 7.0 and elution buffer 50 mM Tris/HCl; 1 M NaCl, pH 9.0.

The conductivity of the green juice extract loaded at 228 cm/h was 4.96 mS/cm. A total of 786 mL was loaded at a flow rate of 3.8 cm/min equivalent to 228 cm/h. Washing and elution was also performed at a flow rate of 3.8 cm/min.

The conductivity of the green juice extract loaded at 450 cm/h was 4.61 mS/cm. A total of 786 mL was loaded at a flow rate of 7.6 cm/min equivalent to 450 cm/h. Washing was at 7.6 cm/min and elution at 3.8 cm/min.

Run through and wash were collected in 4 fractions. The eluate was neutralized to pH 7 by adding 1110 volume of 1 M Tris/HCl, pH 6.5 buffer to the container before collecting the elution fraction. The eluate was collected in one peak.

The amount of haemagglutinin was measured according to the method described in Example 2.

Total protein content was measured according to Bradford.

Results of a haemagglutination assay for both flow rates are given for the run through fractions 1 to 3, a combined run through and wash fraction, and for the combined run through and wash, and eluate in Table 5. Results for the Bradford determination of total protein in the inlet extract, total run through and wash, and eluate are presented in Table 6.

In this experiment a flow rate of 450 cm/h for loading of the extract performed best and resulted in a 45% recovery of haemagglutinating activity relevant to the input green juice extract in a one step binding and elution process.

TABLE 5

Relative haemagglutination activity $C/C_0$ (in %), wherein C is the haemagglutination activity of the outlet fraction (run through 1 to 3, combined run through and wash 4, total run through and wash, or eluate) and $C_0$ of the inlet solution which was set at 100%.

| | | Fraction | | | | |
|---|---|---|---|---|---|---|
| | Run through 1 | Run through 2 | Run through 3 | Run through & wash 4 | Total run through & wash | Eluate |
| Flow rate (cm/h) 228 | 0 | 0 | 20 | 22 | 13 | 45 |
| Flow rate (cm/h) 450 | 0 | 0 | 0 | 55 | 20 | 45 |

TABLE 6

Total protein content of the various fractions loaded and eluted at different flow rates.

| Flow rate (cm/h) | Inlet extract | Total run through & wash | Eluate |
|---|---|---|---|
| 228 | 0.11 | 0.05 | 0.15 |
| 450 | 0.11 | 0.03 | 0.19 |

Example 9

Break Through Curve of Pre-Treated Sample at 450 cm/h Flow Rate

The binding of a virus-like particle present in a pre-treated green plant juice extract and obtained according to the method described in Example 3, was measured at a flow rate of 450 cm/h in a one step binding process in expanded bed adsorption mode, essentially as described in Example 8. All experimental conditions were similar to those used in Example 8 except that the conductivity of the initial extract after dilution was 5.36 mS/cm and the extract was acid precipitated and filtrated before application to the one step binding process in expanded bed adsorption mode. Two independent experiments were performed.

Results of a haemagglutination assay for both experiments are given for the run through fractions 1 to 3, a combined run through and wash fraction, and for the combined run through and wash, and eluate in Table 7. Results for the Bradford determination of total protein in the inlet extract, total run through and wash, and eluate are presented in Table 8. In this experiment the capture of virus-like particles from green plant juice extracts as measured using a haemagglutination assay was 100% in a one step binding and elution process.

TABLE 7

Relative haemagglutination activity $C/C_0$ (in %), wherein C is the haemagglutination activity of the outlet fraction (run through 1 to 3, combined run through and wash 4, total run through and wash, or eluate) and $C_0$ of the inlet solution which was set at 100%. Flow rate was 450 cm/h.

| | | Fraction | | | | | |
|---|---|---|---|---|---|---|---|
| | | Run through 1 | Run through 2 | Run through 3 | Run through & wash 4 | Total run through & wash | Eluate |
| Experiment | 1 | 0 | 0 | 0 | 0 | 0 | 100 |
| | 2 | 0 | 0 | 0 | 0 | 0 | 100 |

TABLE 8

Total protein content of the various fractions loaded and eluted at 450 cm/h flow rate.

| | | Total protein (mg/mL) | |
|---|---|---|---|
| Experiment | Inlet extract | Total run through & wash | Eluate |
| 1 | 0.07 | 0.02 | 0.16 |
| 2 | ND | ND | ND |

ND, not determined.

Example 10

Large Scale Capture of Virus-Like Particles Using Expanded Bed Chromatography Extract. 7,500 *N. benthamiana* plants are infiltrated as described (D'Aoust et al. (2008), supra) to generate 250 kg crude biomass containing haemagglutinin H5 virus-like particles. Following infiltration, plants are incubated in the greenhouse for 6 days before harvesting. Upon harvesting of leaves the biomass is kept overnight at 4° C. in the dark and is homogenized using a screw press (Vincent CP-4) at 15-20 kg/hr using at least 45-psi pressure on the cone essentially as described in Example 3. The green juice is collected and sodium metabisulfite is added to the green juice to a final concentration of 10 mM. Conductivity is measured and the extract is diluted with water before use to a final conductivity of approximately 10. The extract is kept at room temperature. Total volume after dilution is approximately 1,250 L extract.

Column properties. Bead composition: epichlorohydrin cross-linked agarose (4% w/v). Core: tungsten carbide (occupying approximately 10-15% of the volume of the bead). Ligand: DEAE ion exchanger. Mean diameter of the particles: 50 µm. Average density of the adsorbent particles: 16 kg/L. Column diameter: 45 cm. Void volume in sedimented status: approximately 40% of packed volume. Total volume: 63 L adsorbent material is added to a 45 cm diameter column. The column is equilibrated with 5 column volumes of 0.5 M Tris-Cl buffer, pH7 followed by 10 column volumes of 10 mM Tris-Cl buffer, pH7.

Loading. Loading is performed by pumping upward the 1,250 L extract at a flow rate of 450 cm/h, equivalent to 653 L/h essentially as described in Examples 8 and 9. The expansion factor is kept at 2.0-2.5 and unbound material is washed out with 10 mM Tris/HCl, pH7 at the same expansion rate.

Elution. Influenza virus-like particles are recovered by elution with 50 mM Tris-Cl and 1M NaCl, pH9 at an expansion rate of 1.2. Eluted fractions are neutralized by adding ⅒ volume of 1M Tris/HCl, pH 6.5 to the container before collecting the elution peak. Fractions containing virus-like particles comprising haemagglutinin as measured according to the method of Example 2 are pooled for further capture and purification.

Performance monitoring. Chromatography performance is monitored by measurement of UV absorption at 280 nm and 600 nm, conductivity and pH. The capture of virus-like particles containing haemagglutinin H5 is quantitatively measured by ELISA and haemagglutination as described in Example 2 or according to D'Aoust et al. (2008, supra). A Bradford assay is used to determine the total protein content of the fractions. SDS-PAGE is used to establish purity and Western blotting for identification and characterization using haemagglutinin H5-specific antibodies as described in Example 2 and by D'Aoust et al. (2008, supra).

Example 11

Cleaning and Regeneration of Expanded Bed Column

After elution the resin is cleaned and regenerated by washing with 4 column volumes of 0.5 M NaOH, followed by 4 column volumes of distilled water. Re-equilibration is done in 10 mM Tris-Cl buffer, pH7.

Example 12

Further Optimization

*N. berithamiana* plants expressing H5-VLP harvested six days after agro-infiltration are kept overnight at 4° C. in the dark. The plant biomass, including leaves and stems, is homogenized using a screw press (Green Star Corrupad, GS 1000, Korea Co.). MBS is added to 10 mM final concentration to avoid sample oxidation. The crude juice obtained from the screw press is quickly adjusted to pH 5.3 using 20% diluted acetic acid. Extract is left at room temperature for 20-30 min without stirring for partial clarification. Filtration is performed through a Whatman filter paper pre-coated with 3 mm high Celpure P300 (10% Celpure P300 slurry in MBS 10 mM). Vacuum was kept at 508 mbar. Celpure P300 (10%) is added to the extract and mixed for 1 minute. Finally the extract is filtered gently adding extract-celpure slurry by portions (no more than 2 cm liquid phase over the filtration cake). Four potential absorbents are selected and their binding conditions are optimized under static binding conditions in batch mode. The results in Table 9 show that the binding capacity of ionic exchanger adsorbents are affected by two factors: (i) a low ionic strength (2.3 mS/cm or less) and hence (ii) a high volume of plant extract per unit mass of adsorbent (1 g adsorbent to 20 ml of the extract).

Additional experiments are performed in batch mode under static binding conditions to investigate bead size and the incorporation of an initial negative adsorption step in the process. In one experiment, a first step of negative absorption is applied using particles comprising the ligand polyethylenimine (PEI) at dimensions in the range of less than 250 μm, which is followed by a second step of positive absorption onto PEI particles at <50 μm. It is demonstrated that >50% soluble protein impurities and color can be removed from clarified extracts using PEI with a mean particle size of 150 μm, and that H5-VLP's only absorb to absorbents of small particle size. The dilution of the extract is also optimized to a ratio between 1:10 and 1:20 wherein 100% of the H5 is absorbed while in a ratio 1:40 only 70% of the H5 is bound. Nevertheless, although PEI could be considered as a good absorbent, the elution of H5-VLP's was less than optimal.

In another experiment in batch mode under static binding conditions, DEAE dextran is used for optimization in the one-step and the two-step methods. It is shown that about 87% of H5-VLP's can be absorbed on to the DEAE ion exchange beads with a mean dimension of about 50 μm. However, in the one-step binding process, elution of VLP's is poor. In a second experiment, a first negative absorption step with PEI beads is applied which is followed by a second positive absorption step using DEAE dextran beads, 17% of the VLP's are eluted and recovered.

Further experiments are then performed using the two-step process. In one experiment, the homogenized plant material (also referred to as green juice) is diluted five times in water resulting in a conductivity of 5.9 mS/cm and filtered using Celpure 3000. A PEI ion exchange resin is used as an adsorbent at a ratio of 1 g adsorbent to 15 ml of green juice to remove pigments and impurities from the plant material. The PEI ion exchange resin has a mean particle size of 150 μm at pH7. The second step involves flowing the tobacco materials obtained in this manner in expanded bed mode under flow conditions using DEAE ion exchanger with a mean particle size of about 50 μm, a bed height of 15 cm, a flow rate of 3.8 cm/min, and a elution buffer (50 mM Tris and 1 M NaCl pH9). The run through and wash is collected and the resin comprising the VLPs is neutralized to pH7 by adding ⅒ volume of 1M Tris/HCl pH6.5 prior to collecting the eluate as a single peak. The eluate provided a yield of haemagglutinin at 67% (relative to 100% in the starting material). In another experiment, the homogenized plant material is used without filtering, and employing the two-steps process under the same conditions, 22% of the total haemagglutinin is recovered in the eluate but 13% is detected in the run through and wash fraction.

All publications mentioned in the above specification are herein incorporated by reference. Various modifications and variations of the invention will be apparent to those skilled in the art without departing from the scope and spirit of the invention. Although the invention has been described in connection with suitable embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

TABLE 9

| | VLP/H5 bound (%) (*) | Ratio absorbent-to-extract | Conductivity | pH |
|---|---|---|---|---|
| Fast line SP ion exchanger | 70 | 1:20 | 2.39 | 5 |
| QAE dextran based ion exchanger | 96 | 1:20 | 2.3 | 7 |
| Fast line PEI ion exchanger | 100% | 1:20 | 2.3 | 7 |
| DEAE ion exchanger | 100% | 1:20 | 2.2 | 7 |

The invention claimed is:
1. A method for capturing virus like particles of interest from a mixture comprising an extract of disrupted cells of a plant, wherein said method comprises the steps of:
   (i) providing an expanded bed of adsorbent, wherein the density of the adsorbent is in a range from about 2.5 g/ml to about 3.5 g/ml, and wherein the average adsorbent particle size is in a range from about 25 micrometers to about 100 micrometers;

(ii) equilibrating a resin material comprising the expanded bed of adsorbent at a pH in a range from about pH 6.0 to about 8.0; and (iii) loading the mixture onto a column comprising the resin material at a flow rate in a range from about 2 cm/min to about 8 cm/min to bind the virus like particles and wherein the degree of expansion of the expanded bed in the column is in a range from about 1 to about 5, wherein the extract is not pre-treated such that the particles of interest can be isolated in a one-step binding and elution process.

2. The method according to claim 1, wherein the virus like particles comprises a protein of an influenza virus.

3. The method of claim 1, wherein the adsorbent comprises beads that comprise a polysaccharide selected from the group consisting of cellulose, agarose and dextran and derivatives thereof or a combination of two or more thereof.

4. The method according to claim 1, wherein the virus like particles comprise a haemagglutinin.

5. The method claim 1, wherein the mixture comprises disrupted cells of a tobacco plant infiltrated with nucleic acid molecules that express a protein transiently in the plant, said protein being present in the virus like particles.

6. The method according to claim 1, wherein the adsorbent comprises beads that comprise a material selected from the group consisting of plastics, methacrylate, an anion exchanger, diethylaminoethyl, a cation exchanger, a polysaccharide, silica, poly(styrenedivinyl)benzene, polyacrylamide, ceramic and derivatives thereof or a combination of two or more thereof.

7. The method according to claim 1, wherein the beads comprise an inert core that comprises a material selected from the group consisting of: quartz; silica;
Nd-Fe-B alloy; stainless steel; zirconium oxide; zirconia; metal silicates; metal borosilicates; ceramics; metal oxides and sulfides; non-metal oxides; metal salts; metallic elements; and alloys of metallic elements; and derivatives thereof or a combination of two or more thereof.

8. The method according to claim 1, wherein said method comprises a pre-capture step which comprises the use of a first expanded bed of adsorbent.

9. The method according to claim 1, wherein the adsorbent comprises a ligand.

10. The method according to claim 1, wherein the conductivity of the mixture prior to contact with the adsorbent is between about 1 mS/cm to 10 mS/cm;
and/or the pH of the mixture prior to contact with the adsorbent is between about pH 6.0 to pH 8.0.

11. A method for capturing virus like particles of interest from a mixture comprising an extract of disrupted cells of a plant, the method comprising the steps of:
(i) providing an expanded bed of adsorbent comprising diethylaminoethyl cellulose dextran in a column, wherein the density of the adsorbent is between about 2.5 g/ml and 3.5 g/ml, and wherein the average adsorbent particle size is about 50;
(ii) equilibrating a resin material comprising the expanded bed of adsorbent at a pH in the range of about pH 6.0 to 8.0;
(iii) providing a mixture comprising disrupted cells of tobacco plant material, wherein said mixture has a conductivity of between about 2 mS/cm to 3 mS/cm;
(iv) loading the mixture onto a column comprising the resin material at a flow rate of about 2.5 cm/min to bind the virus like particles and wherein the degree of expansion of the expanded bed in the column is about 2;

(v) washing the loaded column using a buffer having a pH in the range of about pH 6.0 to 8.0; and (vi) eluting the bound particle of interest from the column in one or more fractions, wherein the extract is not pre-treated such that the particles of interest can be isolated in a one-step binding and elution process.

12. The method of claim 11, wherein step (iii) comprises (a) providing whole tobacco plants that are transiently expressing a protein that is present in the virus like particles; (b) disrupting cells of the leaves and stems of the tobacco plants to produce the tobacco plant material; and (c) adjusting the pH and conductivity of the mixture by dilution with a buffer or deionized water.

13. A mixture comprising an expanded bed of adsorbent and disrupted plant cells comprising a virus like particle, wherein the virus like particle is reversibly bound to the expanded bed of adsorbent.

14. The method according to claim 1, wherein the virus like particles comprise a haemagglutinin subtype selected from the group consisting of H1, H2, H3, H4, H5, H6, H7, H8, H9, H10, H11, H12, H13, H14, H15 or H16 or a combination of two or more thereof.

15. The method according to claim 1, wherein the cells are derived from aerial parts of the plant.

16. The method according to claim 1 comprising the additional step of washing the loaded column using a buffer having a pH in the range of about pH 6.0 to 8.0.

17. The method according to claim 1, comprising the additional step of eluting the bound particle of interest from the column in one or more fractions.

18. The method according to claim 8, wherein the size of the beads is between about 125μm and 250μm.

19. The method according to claim 9, wherein the ligand is selected from the group consisting of (i) benzylamine or a derivative thereof; (ii) an alkylamine or a derivative thereof; (iii) an alkenylamine or a derivative thereof; (iv) an alkynylamine or a derivative thereof; (v) an alkoxyamine or a derivative thereof; and (vi) an amine of mono- or bicyclic aromatic or heteroaromatic moities or a derivative thereof, or a combination of two or more thereof; or wherein the ligand comprises an anion exchange resin; wherein the anion exchange resin comprises a diethylaminoethyl cellulose-based ion exchange resin or comprises, consists or consists essentially of diethylaminoethyl cellulose dextran-based ion exchange resin.

* * * * *